(12) United States Patent
Vetter

(10) Patent No.: US 11,234,935 B2
(45) Date of Patent: Feb. 1, 2022

(54) METHOD OF INDUCING SATIETY

(71) Applicant: PERORA GMBH, Heidelberg (DE)

(72) Inventor: Dirk Vetter, Heidelberg (DE)

(73) Assignee: PERORA GMBH, Heidelberg (DE)

( * ) Notice: Subject to any disclaimer, the term of this patent is extended or adjusted under 35 U.S.C. 154(b) by 142 days.

(21) Appl. No.: 15/742,359

(22) PCT Filed: Jul. 7, 2016

(86) PCT No.: PCT/EP2016/066218
§ 371 (c)(1),
(2) Date: Jan. 5, 2018

(87) PCT Pub. No.: WO2017/005890
PCT Pub. Date: Jan. 12, 2017

(65) Prior Publication Data
US 2018/0200189 A1    Jul. 19, 2018

Related U.S. Application Data

(60) Provisional application No. 62/203,824, filed on Aug. 11, 2015.

(30) Foreign Application Priority Data

| Jul. 7, 2015 | (EP) | 15175571 |
| Jul. 8, 2015 | (EP) | 15175819 |
| Aug. 11, 2015 | (EP) | 15180659 |
| Aug. 11, 2015 | (EP) | 15180665 |
| Dec. 23, 2015 | (EP) | 15202552 |

(51) Int. Cl.
*A61P 3/04* (2006.01)
*A61K 9/14* (2006.01)
*A61K 9/20* (2006.01)
*A61K 9/50* (2006.01)

(52) U.S. Cl.
CPC .............. *A61K 9/145* (2013.01); *A61K 9/146* (2013.01); *A61K 9/2072* (2013.01); *A61K 9/5078* (2013.01); *A61K 9/5089* (2013.01); *A61P 3/04* (2018.01)

(58) Field of Classification Search
None
See application file for complete search history.

(56) References Cited

U.S. PATENT DOCUMENTS

| 4,009,265 A | 2/1977 | Howard et al. |
| 5,104,677 A | 4/1992 | Behr et al. |
| 5,403,593 A | 4/1995 | Royce |
| 5,571,533 A | 11/1996 | Santus et al. |
| 5,753,253 A | 5/1998 | Meyer |
| 6,368,635 B1 | 4/2002 | Akiyama et al. |
| 6,428,813 B1 | 8/2002 | Akiyama et al. |
| 6,429,190 B1 | 8/2002 | Portman |
| 6,835,397 B2 | 6/2004 | Lee et al. |
| 8,246,985 B2 | 8/2012 | Park et al. |
| 8,962,046 B2 | 2/2015 | Malkki |
| 9,457,048 B2 | 10/2016 | Davis |
| 2002/0012733 A1 | 1/2002 | Kester et al. |
| 2003/0008810 A1 | 1/2003 | Portman |
| 2003/0013679 A1 | 1/2003 | Wolf et al. |
| 2003/0161885 A1 | 8/2003 | Beisel et al. |
| 2003/0170371 A1 | 9/2003 | Jobe et al. |
| 2003/0203004 A1 | 10/2003 | Keim et al. |
| 2004/0126424 A1 | 7/2004 | Jandacek et al. |
| 2004/0258803 A1 | 12/2004 | Van Benthum et al. |
| 2005/0276900 A1 | 12/2005 | Ullanoormadam et al. |
| 2006/0073203 A1 | 4/2006 | Ljusberg-Wahren et al. |
| 2006/0134144 A1 | 6/2006 | Chung et al. |
| 2006/0141053 A1 | 6/2006 | Menjoge et al. |
| 2006/0193907 A1* | 8/2006 | Remmereit ........... A23L 33/175 424/451 |
| 2007/0286909 A1 | 12/2007 | Smith et al. |
| 2008/0044481 A1 | 2/2008 | Harel |
| 2008/0075688 A1 | 3/2008 | Hird et al. |
| 2009/0196848 A1 | 8/2009 | Davis |

(Continued)

FOREIGN PATENT DOCUMENTS

| CN | 1251035 | 4/2000 |
| CN | 1794921 | 6/2006 |

(Continued)

OTHER PUBLICATIONS

"Lauric Acid," as retrieved from the Internet at https://en.wikipedia.org/wiki/Medium-chain_triglyceride on Oct. 15, 2019. (Year: 2019).*
Milk Fat, as retrieved from the Internet at http://www.milkfacts.info-/Milk%20Composition/Fat.html on May 4, 2020. (Year: 2020).*
(Butterfat, as retrieved from the Internet at https://en.wikipedia.org/wiki/Butterfat on May 11, 2020. (Year: 2020).*
Fatty Acids, as retrieved from the Internet at http://chemistry.elmhurst.edu/vchembook-/551fattyacids.html on May 11, 2020. (Year: 2020).*
Carvalho et al., "Mucoadhesive drug delivery systems," Brazilian Journal of Pharmaceutical Sciences, 46(1): 1-17 (2010).
Flint et al., "Reproducibility, power and validity of visual analogue scales in assessment of appetite sensations in single test meal studies," International Journal of Obesity, 24: 38-48 (2000).
International Search Report for International Application No. PCT/EP2016/066214, dated Oct. 11, 2016, 4 pages.

(Continued)

*Primary Examiner* — David J Blanchard
*Assistant Examiner* — Daniel F Coughlin
(74) *Attorney, Agent, or Firm* — Hoxie & Associates LLC

(57) ABSTRACT

The invention provides a method of inducing satiety in a subject comprising a step of orally administering a composition comprising an effective amount of a first agent capable of inducing satiety and of a second agent capable of augmenting the satiety-inducing effect of the first agent. Also disclosed are compositions for carrying out the method and a body weight management system comprising such compositions in combination with a device configured for the collection, storage and/or display of information relating to a subject's response to a predefined therapeutic regimen of orally administering the composition.

19 Claims, No Drawings

(56) References Cited

U.S. PATENT DOCUMENTS

| | | | |
|---|---|---|---|
| 2009/0281039 A1* | 11/2009 | Malkki | A23L 33/30 |
| | | | 514/1.1 |
| 2010/0216740 A1* | 8/2010 | Stahl | A23L 7/198 |
| | | | 514/54 |
| 2011/0027412 A1 | 2/2011 | Spence et al. | |
| 2011/0123609 A1 | 5/2011 | Borude et al. | |
| 2011/0229602 A1 | 9/2011 | Aymard et al. | |
| 2012/0052151 A1 | 3/2012 | Sannino et al. | |
| 2012/0058195 A1 | 3/2012 | Harel | |
| 2014/0234449 A1 | 8/2014 | Nielsen et al. | |
| 2015/0305394 A1 | 10/2015 | Mazer et al. | |
| 2017/0258725 A1 | 9/2017 | Vetter | |
| 2017/0258824 A1 | 9/2017 | Vetter | |
| 2018/0027860 A1 | 2/2018 | Halford et al. | |
| 2018/0185327 A1 | 7/2018 | Vetter | |
| 2018/0214382 A1 | 8/2018 | Vetter | |
| 2018/0214411 A1 | 8/2018 | Vetter | |
| 2018/0228757 A1 | 8/2018 | Vetter | |
| 2019/0110514 A1 | 4/2019 | Vetter | |

FOREIGN PATENT DOCUMENTS

| | | |
|---|---|---|
| DE | 3139920 | 4/1983 |
| EP | 0246294 | 11/1987 |
| EP | 0580861 | 2/1994 |
| EP | 2098222 | 9/2009 |
| JP | H05132416 | 5/1993 |
| JP | H05132416 A | 5/1993 |
| JP | 2000178206 | 6/2000 |
| JP | 2002188095 | 7/2002 |
| JP | 2005046054 | 2/2005 |
| WO | WO 99/38052 | 7/1999 |
| WO | WO 2001/005408 | 1/2001 |
| WO | WO 2001/017377 | 3/2001 |
| WO | WO 2003/037355 | 5/2003 |
| WO | WO 2004/060401 | 7/2004 |
| WO | WO 2005/002430 | 1/2005 |
| WO | WO 2007/123338 | 11/2007 |
| WO | WO 2008/017659 | 2/2008 |
| WO | WO 2009/07131 | 6/2009 |
| WO | WO 2010/059725 | 5/2010 |
| WO | WO 2011/096950 | 8/2011 |
| WO | WO 2011/136975 | 11/2011 |
| WO | WO 2014/066680 | 5/2014 |
| WO | WO 2014/066682 | 5/2014 |
| WO | WO 2014/202997 | 12/2014 |
| WO | WO 2016/014500 | 1/2016 |
| WO | WO 2017/005887 | 1/2017 |

OTHER PUBLICATIONS

International Search Report for International Application No. PCT/EP2016/066216, dated Oct. 14, 2016, 3 pages.

International Search Report for International Application No. PCT/EP2016/066217, dated Oct. 10, 2016, 4 pages.

International Search Report for International Application No. PCT/EP2016/066218, dated Oct. 10, 2016, 4 pages.

International Search Report for International Application No. PCT/EP2016/066220, dated Oct. 10, 2016, 4 pages.

Ivarsson et al., "Comparison of in vitro methods of measuring mucoadhesion: Ellipsometry, tensile strength and rheological measurements," Colloids and Surfaces B: Biointerfaces, 92: 353-359 (2012).

JP2000178206, FANCL Corp, "Lubricant Containing Plant Fat and Oil," Jun. 27, 2000, English language machine translation of abstract, Espacenet, date obtained: Mar. 16, 2018, 1 page <https://worldwide.espacenet.com/publicationDetails/biblio?CC=JP&NR=2000178206A&KC=A&FT=D&ND=3&date=20000627&DB=&locale=en_EP>.

JP2002188095, FANCL Corp, "Vegetable Oil and Fat Powder and Food Composition Containing the Powder," Jul. 5, 2002, English language machine translation of abstract, Espacenet, date obtained: Mar. 16, 2018, 1 page <https://worldwide.espacenet.com/publicationDetails/biblio?II=1&ND=3&adjacent=true&locale=en_EP&FT=D&date=20020705&CC=JP&NR=2002188095A&KC=A>.

JP2005046054, Nippon Kayaku KK, "Diet Food and Pharmaceutical Preparation for Diet," Feb. 24, 2005, English language machine translation of abstract, Espacenet, date obtained: Mar. 16, 2018, 1 page <https://worldwide.espacenet.com/publicationDetails/biblio?II=0&ND=3&adjacent=true&locale=en_EP&FT=D&date=20050224&CC=JP&NR=2005046054A&KC=A>.

WO2001017377, Beisel Günther, "Cross-Linked Agent for Generation of a Long-Lasting Satiety Effect and Method for the Production of the Said," Mar. 15, 2001, English language machine translation of abstract, Espacenet, date obtained: Apr. 3, 2018, 2 pages <https://worldwide.espacenet.com/publicationDetails/biblio?II=0&ND=3&adjacent=true&locale=en_EP&FT=D&date=20010315&CC=WO&NR=0117377A1&KC=A1>.

"Cholecystokinin," Wikipedia, retrieved from the web Jun. 13, 2019, 8 pages, URL: <https://en.wikipedia.org/wiki/Cholecystokinin>.

Feltrin, K.L., et al., "Acute oral administration of lauric acid reduces energy intake in healthy males," e-SPEN Journal, 9: e69-e75 (2014).

CN1251035, Takeda Chemical Ind. Ltd., "Gastrointestinal mucosa-adherent pharmaceutical composition," Apr. 19, 2000, English language machine translation of abstract, Espacenet, date obtained: Mar. 27, 2019, 1 page <URL: https://worldwide.espacenet.com/publicationDetails/biblio?II=0&ND=3&adjacent=true&locale=en_EP&FT=D&date=20000419&CC=CN&NR=1251035A&KC=A>.

CN1794921, Unilever NV, "Satiety enhancing food products," Jun. 28, 2006, English language machine translation of abstract, Espacenet, date obtained: Mar. 27, 2019, 1 page <URL: https://worldwide.espacenet.com/publicationDetails/biblio?II=0&ND=3&adjacent=true&locale=en_EP&FT=D&date=20060628&CC=CN&NR=1794921A&KC=A>.

Hermsdorff, HH, et al., "Macronutrient profile affects diet-induced thermogenesis and energy intake," Arch Latinoam Nutr., 57(1): 33-42 (2007) (Abstract Only).

International Search Report for International Application No. PCT/EP2017/053713, dated Apr. 28, 2017, 5 pages.

Makarova, S.G., et al., "Long-Chain Polyunsaturated ω-3 and ω-6 Fatty Acids as Essential Nutrients in Different Periods of Childhood," Pediatric pharmacology, 10(4): 80-88 (2013) (Russian Translation Only).

"MediSafe introduces medication reminder smartwatch," Jul. 14, 2014, EMS1, date obtained: Jan. 14, 2019, 2 pages <https://www.ems1.com/ems-products/apparel-accessories/articles/1945312-MediSafe-introduces-medication-reminder-smartwatch/>.

Rowe, R.C., et al., Handbook of Pharmaceutical Excipients, 6: 685-686 (2009).

International Search Report for International Application No. PCT/EP2015/068501, dated Sep. 22, 2015, 4 pages.

International Search Report for International Application No. PCT/EP2015/068502, dated Sep. 22, 2015, 4 pages.

Alleleyn, A., et al., "Gastrointestinal Nutrient Infusion Site and Eating Behavior: Evidence for a Proximal to Distal Gradient within the Small Intestine?" Nutrients, 8 (117): 1-15 (2016).

JPH05132416, Takeda Chemical Industries Ltd., "Matrix Adherent to Mucosa of Alimentary Tract, Preparation and Coating Agent," May 28, 1993, English language machine translation of abstract, Espacenet, date obtained: May 14, 2019, 1 page <https://worldwide.espacenet.com/publicationDetails/biblio?II=0&ND=3&adjacent=true&locale=en_EP&FT=D&date=19930528&CC=JP&NR=H05132416A&KC=A>.

Sato, S., et al., "Clinical comparison of branched-chain amino acid (L-Leucine, L-Isoleucine, L-Valine) granules and oral nutrition for hepatic insufficiency in patients with decompensated liver cirrhosis (LIV-EN study)," Hepatology Research, 31: 232-240 (2005).

Guerin-Deremaux, et al., "The soluble fibre NUTRIOSE induces a dose-dependant beneficial impact on satiety over time in humans," Nutrition Research, 31:665-672 (2011).

Lehranc-Millot, et al., "Impact of a Resistant Dextrin on Intestinal Ecology: How Altering the Digestive Ecosystem with NUTRIOSEO,

(56) References Cited

OTHER PUBLICATIONS a Soluble Fibre with Prebiotic Properties, May Be Beneficial for Health," The Journal of International Medical Research, 40:211-224 (2012).

Chapman, et al., "Effects of small-intestinal fat and carbohydrate infusions on appetite and food intake in obese and nonobese men," Original Research Communications, American Journal of Clinical Nutrition, 69:6-12 (1999).

DE 3139920, Nittner Erich, "Agent in the for of granules based on polysaccharide gums, process for the preparation thereof and use," Apr. 28, 1983, English language machine translation, Espacenet, date obtained: Sep. 25, 2020, 1 page. <https://worldwide.espacenet.com/patent/search/family/006143620/publication/DE3139920A1?q=DE3139920>.

Del Carmen, J., "Nutritionists should consider U.S. soybean meal's mineral content when differentiating between origins," USSEC, 1-3 (2019).

Guthmann, "Pellet Formulations," 4, 33-36.

Lu, et al., "Postprandial inhibition of gastric ghrelin secretion by long-chain fatty acid through GPR120 in isolated gastric ghrelin cells and mice," Am J Physiol Gastroinstest Liver Physiol., 303(3):G367-G376 (2012).

\* cited by examiner

METHOD OF INDUCING SATIETY

CROSS-REFERENCE TO RELATED APPLICATIONS

This application is a U.S. National Stage Application under 35 USC 371 of International Application No. PCT/EP2016/066218 filed on Jul. 7, 2016, which claims priority to, and the benefit of, European Application No. 15175571.7, filed Jul. 7, 2015, European Application No. 15175819.0, filed Jul. 8, 2015, European Application No. 15180665.0, filed Aug. 11, 2015, U.S. Provisional Application No. 62/203,824, filed Aug. 11, 2015, European Application No. 15180659.3, filed Aug. 11, 2015, and European Application No. 15202552.4, filed Dec. 23, 2015, the contents of each of which are incorporated herein by reference in their entireties.

FIELD

The present invention relates to oral compositions for the delivery of bioactive agents to the gastrointestinal tract.

BACKGROUND

Numerous invasive methods and systems are known for use in the treatment and/or prevention of obesity. For instance, WO 2011/136975 A1 describes gastric bands, and in particular a method and system for displaying gastric band information which can support adjustment of the gastric band. The adjustment of the gastric band may be dependent on several pieces of data such as satiety state data.

Alternative non-invasive approaches for the treatment of obesity may infer satiety or the feeling of fullness or satisfaction through a variety of different ingestible compositions such as gelling systems, swelling or expandable systems or certain nutrient compositions.

It is an object of the present invention to provide an effective method for delivering fatty acids and lipids based on fatty acids to the gastrointestinal tract. A further object is to provide means for the delivering such fatty acids and lipids to specific regions within the gastrointestinal tract, such as the stomach or the duodenum. A further object is to provide compositions, dosage forms and/or formulations which are useful for the oral delivery of fatty acids and lipids based on fatty acids. A yet further object is to provide a method for the treatment and/or prevention of obesity and diseases or conditions associated with obesity.

Further objects will become apparent on the basis of the following description including the examples, and the patent claims.

SUMMARY OF THE INVENTION

In a first aspect, the invention provides an oral composition comprising an effective amount of a first agent capable of inducing satiety, a second agent capable of augmenting the satiety-inducing effect of the first agent. The first agent which is capable of inducing satiety may be selected from medium or long chain fatty acid compounds, e.g. derivable from fatty acid glyceride components. The second agent may represent a polymer capable of increasing the bioavailability of the first agent in the gastrointestinal tract, such as a water-soluble polysaccharide component.

The composition may comprise a plurality of edible particles comprising the first and the second agent, wherein the second agent prolongs the integrity of the particles and/or accelerates the gastric emptying of the particles after oral administration and—where required—mastication of the oral composition.

In another aspect, the invention provides an ingestible particle having a sieve diameter in the range from 0.01 mm to 10 mm, comprising an intimate mixture of (a) at least 10 wt.-% of a water-soluble polysaccharide component based on glucose or fructose having an average degree of polymerisation from 2 to 100, or from 4 to 80, and (b) at least 10 wt.-% of a fatty acid glyceride component having a melting point of higher than 37° C., wherein the particle comprises not more than 5 wt.-% of mucoadhesive polymer.

In another aspect, the invention provides an ingestible particle having a sieve diameter in the range from 0.01 mm to 10 mm, comprising an intimate mixture of (a) at least 10 wt.-% of a water-soluble polysaccharide component based on glucose or fructose having an average degree of polymerisation from 2 to 100, or from 4 to 80, and (b) at least 10 wt.-% of a fatty acid glyceride component having a melting point of higher than 37° C., wherein the combined content of the water-soluble polysaccharide component and of the fatty acid glyceride component in the particle is at least 80 wt.-%.

In an alternative embodiment of the invention, the water-soluble polysaccharide component in the ingestible particles may be replaced by a water-insoluble, non-swelling, edible polysaccharide component, preferably a polysaccharide component which is resistant to digestion in the human small intestine, such as cellulose, hemicellulose, or long-chain and/or branched beta-glucans like curdlan. In this case, the ingestible particles having a sieve diameter in the range from 0.01 mm to 10 mm may comprise an intimate mixture of (a) at least 10 wt.-% of a water-insoluble, non-swelling, edible polysaccharide component, and (b) at least 10 wt.-% of a fatty acid glyceride component having a melting point of higher than 37° C., wherein the ingestible particle comprises not more than 5 wt.-% of mucoadhesive polymer, and/or wherein the combined content of the water-insoluble, non-swelling, edible polysaccharide component and of the fatty acid glyceride component in the particle is at least 80 wt.-%, The particles may be substantially free of mucoadhesive polymers. Optionally, the particles may essentially consist of the polysaccharide component and the fatty acid glyceride component and optionally one or more further excipients without mucoadhesive properties, such as sugars, sugar alcohols, vitamins, amino acids, proteins and/or micronutrients.

The water-soluble polysaccharide component may exhibit a solubility of at least 2 wt.-%, and optionally of at least 5 wt.-%, in purified water at 25° C. The water-soluble or water-insoluble polysaccharide component may comprise a neutral polysaccharide that is resistant to digestion in the human small intestine. Examples of suitable water-soluble polysaccharide components include dextrins, inulins and glucans such as beta-glucans; in particular dextrins having a degree of polymerisation from 2 to 100, preferably from 4 to 40, or from 5 to 40, or from 8 to 40, in particular from 10 to 30 and further preferably from 12 to 25; or inulins having a degree of polymerisation from 2 to 100, preferably from 4 to 60, or from 10 to 60, more preferably from 3 to 50, or from 4 to 30, or from 5 to 25, or soluble cereal-derived beta-glucans like oat- or barley beta-glucan. Examples of suitable water-insoluble, non-swelling, edible polysaccharide components include cellulose, hemicellulose, or long-chain and/or branched beta-glucans like curdlan.

The fatty acid glyceride component may have a melting point from 38° C. to 75° C., in particular from 40° C. to 70° C. The fatty acid glyceride component may comprise fatty acid triglycerides; the content of the fatty acid triglyceride in the particle being at least 10 wt.-%.

The particle may e.g. comprise a water-soluble polysaccharide component comprising a resistant dextrin derived from wheat or maize starch, and a fatty acid glyceride component comprising a fractionated but non-hydrogenated palm stearin or palm kernel stearin.

The particles according to the invention may be in the form of a granule, a pellet, or a minitablet. The particles according to the invention may have a mass median sieve diameter in the range from 0.01 mm to 10 mm.

In a further aspect, the invention provides a method for the preparation of the particle according to the invention comprising the steps of (i) preparing an intimate mixture comprising the water-soluble polysaccharide component, or alternatively a water-insoluble, non-swelling, edible polysaccharide component, and the fatty acid glyceride component, and (ii) processing the intimate mixture to obtain ingestible particles of said mixture by extrusion using a screw extruder; spray congealing; melt granulation; compression into minitablets; melt injection into a liquid medium; or spray coating onto inert cores.

In a further aspect, the invention provides compositions for oral administration which comprise the ingestible particles or which are prepared from them, such as vials, bottles, sachets, stick packs, capsules or tablets or other dosage units.

Single dose units or packages may be provided comprising these particle compositions for oral administration, wherein the amount of the composition is from 3 g to 20 g, and/or wherein the amount of the fatty acid glyceride component in the composition is at least 1 g, preferably at least 2 g.

Optionally, the composition for oral administration may comprise the ingestible particles together with one or more additional "extragranular" components selected from components A to E, which may either be combined with the ingestible particles in the same primary packaging or dosage form as a 'ready-to-use' composition, or provided separately from said particles—e.g. in the form of a kit—such that the consumer, or user, may add it to the solid phase prior to ingestion.

Component A comprises a native or modified protein; component B comprises a native or modified dietary fibre; component C comprises a vitamin, a micro-nutrient such as a micro-mineral, an organic acid, choline, cholesterol, and/or a further dietary element (also called mineral nutrients); component D comprises at least one amino acid; and component E comprises one or more substance(s) for improved flavour. Components A to E may optionally be provided in the form of a powder, a powder blend and/or a granulate.

In a yet further aspect, the invention provides the use of the particles and of the compositions based on the particles for the prevention and/or treatment of obesity, or a disease or condition associated with obesity. Moreover, the use in appetite suppression and induction of satiety is provided.

Moreover, the invention provides a method for inducing satiety in a subject; a method of treating or preventing overweight, obesity, or a disease or condition associated with overweight or obesity in a subject; and a method of controlling or reducing the body weight of a subject; which methods comprise a step of orally administering a composition comprising an effective amount of the first agent capable of inducing satiety and of the second agent capable of augmenting the satiety-inducing effect of the first agent.

Optionally, the use may be associated with a dietary schedule according to which a single dose of the ingestible particles of the invention and/or of the compositions comprising them is administered orally to a human subject at least once a day over a period of at least one week for this purpose. Further optionally, the human subject may be instructed to substitute a meal, partially or entirely, with said administration.

The invention furthermore provides a body weight management system comprising such composition and a device configured for the collection, storage and/or display of information relating to a subject's adherence, or the effectiveness of, a predefined therapeutic regimen of orally administering the composition.

DETAILED DESCRIPTION OF THE INVENTION

In a first aspect, an oral composition comprising an effective amount of a first agent capable of inducing satiety, a second agent capable of augmenting the satiety-inducing effect of the first agent. The first agent may be any compound or mixture of compounds which, after oral ingestions by a subject, triggers a signal or signalling cascade causing the subject to experience a feeling of satiety, or a reduced feeling of hunger or appetite. The second agent, on the other hand, may be any compound or mixture of compounds which, given by itself, does not induce a feeling of satiety, but when co-administered with the first agent, is capable of augmenting the satiety-inducing effect of the first agent.

The augmentation may be achieved by a direct or indirect interaction, and effected via any pharmacological, physiological, or physical means. For example, a compound or mixture of compounds may be selected as the second agent which is capable of increasing the bioavailability of the first agent which induces satiety. Alternatively or in addition, the second agent may be selected such as to enhance the gastric emptying of the composition. In one embodiment, the composition comprises a plurality of edible particles comprising the first and the second agent, wherein the second agent prolongs the integrity of the particles and thereby accelerates the gastric emptying of the particles after oral administration and—where required—mastication of the oral composition.

The increase in bioavailability of the first agent in the upper gastrointestinal tract may optionally be effected by the second agent in that the second agent increases the integrity of the oral composition. Depending on the actual compounds selected as first and second agents, respectively, this may best be accomplished by providing a composition for oral administration in which effective amounts of the first agent and the second agent are incorporated as an intimate mixture.

In a preferred embodiment, the first agent is a medium or long chain fatty acid glyceride compound, as defined below, or a mixture of two or more medium or long chain fatty acid glyceride compounds. The second agent is preferably a water-soluble polysaccharide component, as described in more detail below.

In another aspect, the invention provides an ingestible particle having a sieve diameter in the range from 0.01 mm to 10 mm, comprising an intimate mixture of (a) at least 10 wt.-% of a water-soluble polysaccharide component based on glucose or fructose having an average degree of polymerisation from 2 to 100, or from 4 to 80 (hereafter referred to as 'the polysaccharide component'), and (b) at least 10 wt.-% of a fatty acid glyceride component having a melting point of higher than 37° C. (hereafter referred to as 'the fatty acid glyceride component'), wherein the particle comprises not more than 5 wt.-% of mucoadhesive polymer.

In another aspect, the invention provides an ingestible particle having a sieve diameter in the range from 0.01 to 10 mm, comprising an intimate mixture of (a) at least 10 wt.-% of a water-soluble polysaccharide component based on glucose or fructose having an average degree of polymerisation from 2 to 100, or from 4 to 80, and (b) at least 10 wt.-% of a fatty acid glyceride component having a melting point of higher than 37° C., wherein the combined content of the water-soluble polysaccharide component and of the fatty acid glyceride component in the particle is at least 80 wt.-%.

In an alternative aspect of the invention, the water-soluble polysaccharide component in the embodiments described above may be replaced by a water-insoluble, non-swelling, edible polysaccharide component (also referred to hereafter as the 'polysaccharide component' unless specified otherwise); like e.g. cellulose, hemicellulose or long-chain and/or branched beta-glucans like curdlan. According to this embodiment, the invention provides an ingestible particle having a sieve diameter in the range from 0.01 mm to 10 mm, comprising an intimate mixture of (a) at least 10 wt.-% of a water-insoluble, non-swelling, edible polysaccharide component, and (b) at least 10 wt.-% of a fatty acid glyceride component having a melting point of higher than 37° C., wherein the particle comprises not more than 5 wt.-% of mucoadhesive polymer, and/or wherein the combined content of the water-insoluble, non-swelling, edible polysaccharide component and of the fatty acid glyceride component in the particle is at least 80 wt.-%.

Unless specified otherwise, the terms 'the mixture' or 'the intimate mixture' herein refers to the mixture according to the invention as described above; i.e. intimately mixed blends of the specific polysaccharide component(s) and the specific fatty acid glyceride component(s), with a combined polysaccharide/fatty acid glyceride content of at least 80 wt.-% and not more than 5 wt.-% of mucoadhesive polymer.

According to the invention, the polysaccharide component is in an intimate mixture with the fatty acid glyceride component. This means that one component, usually the polysaccharide component, may be largely dispersed within the other component, usually the fatty acid glyceride component, whether molecularly, colloidally or in the form of a solid suspension; i.e. the polysaccharide component(s) and the fatty acid glyceride component(s) are inseparably blended into one coherent solid phase, regardless of how this coherence and/or inseparability are achieved. The fatty acid glyceride component may form a continuous phase in which the polysaccharide component is discontinuous and in dispersed form. For the avoidance of doubt, this does not exclude that some of the polysaccharide component is not fully dispersed, but positioned at the outer surface of the lipid component.

Alternatively—and depending on the specific ratio of the components to each other, as well as the method of forming the mixture—both components may be dispersed by/in each other with no clear distinction between continuous and discontinuous phase. The main requirement of an intimate mixture is that the mixture is relatively homogenous, as will be understood by the skilled person.

Examples of intimate mixtures according to the invention include melts of the fatty acid glyceride component into which the polysaccharide component is mixed prior to cooling down, as well as any co-processed mixture in which one component (commonly the polysaccharide) is embedded in and/or coated with the other (commonly the fatty acid glyceride component). Examples of what is not considered an intimate mixture according to the invention include uncompressed powder blends of the two components, because such powder blends may in theory be separated and thereby lose their homogeneity (e.g. one component being wetted by an ingestible liquid, while the other is poorly wetted and may exhibit floatation).

It should further be understood that, as used herein, the terms 'a' or 'an' or 'the' or features described in their singular form do not exclude a plurality of the respective features. Unless explicitly stated or described otherwise, expressions such as "an water-soluble polysaccharide component", "a fatty acid glyceride component" or the like are chosen solely for reasons of simplicity and are meant to encompass one or more water-soluble polysaccharide component(s), fatty acid glyceride component(s), etc.; e.g. in the form of blends, or mixtures, of two or more of the respective components.

All percentages, parts and ratios as used herein, are by weight of the total formulation, unless otherwise specified; i.e. "%" should be read as "wt.-%" unless otherwise specified or unless it is clear from the context that another type of percentage is meant.

Optionally, the ingestible particles may be provided in compositions for oral administration; for instance in oral compositions together with one or more additional "extragranular" components selected from components A to E, which may either be combined with the ingestible particles in the same primary packaging or dosage form as a 'ready-to-use' composition, or provided separately from said particles—e.g. in the form of a kit—such that the consumer, or user, may add it to the solid phase prior to ingestion. It is to be understood that the term "extragranular" is used in the widest sense and is not intended to imply, that all ingestible particles are necessarily prepared by a granulation step.

Component A comprises a native or modified protein; component B comprises a native or modified dietary fibre; component C comprises a vitamin, a micro-nutrient such as one or more micro-minerals, organic acids, choline, cholesterol, and/or a further dietary element (also called mineral nutrients); component D comprises at least one amino acid; and component E comprises one or more substance(s) for improved flavour. Components A to E may optionally be provided in the form of a powder, a powder blend and/or a granulate. More details on components A to E will be provided further below.

The term 'kit' as used herein means that the components comprised in said kit are provided physically separable and distinguishable from one another as different components but are sold together for the purpose of being administered, or used, together, though not necessarily simultaneously. The kit may for instance be supplied in the form of:

a) separate compartments of one primary package (such as a sachet divided into two or more 'sub-pouches' by a laminating seam, or a glass vial filled with one kit component and the other kit component being held in the screw-top lid of said glass vial);

b) separate primary packages packaged together within one secondary package (such as separate sets of sachets for two or more kit components, the two or more sachet-sets being sold in one and the same folded box);

c) separate primary packages packaged in two or more separate secondary packages which are in turn held together by paper or plastic wrappers, ribbons, sleeves or the like (such as separate sets of sachets for two or more kit components, the two or more sachet-sets being sold in two or more card-board boxes, the latter being wrapped with a shrink foil wrapper); or d) combinations thereof (such as a first kit-component being provided in multiple-dose card-board drum, optionally with a dosing spoon, the card-board drum being sold in a folded box together with a multitude of foil-wrapped single-serving sized portions of a second kit-component).

Optionally, the kits of the invention may be further comprise written instructions on how to best, or preferably, combine and use the two or more kit components.

The inventors have found that the ingestible particles as defined herein, and in particular oral compositions comprising or prepared from a plurality of the particles, are capable of effectively inducing satiety, of suppressing the appetite, and therefore may be used to prevent and/or treat obesity or conditions associated with obesity; e.g. by using the ingestible particles as defined herein and/or compositions comprising or prepared from a plurality of these particles for body weight reduction.

Without wishing to be bound by theory, it is currently believed that upon oral administration, the fatty acid or fatty acid ester comprised in the particle is more effectively delivered to the mucosa of the gastrointestinal tract, such as the stomach or duodenum, and in particular to the receptors in the upper intestinal mucosa which are involved in the signalling of satiety, by virtue of the water-soluble or water-insoluble polysaccharide component, which may be instrumental in providing a prolonged or otherwise increased interaction of the fatty acid material with target structures at/in the mucosa. Without wishing to be bound by theory, this increase in bioavailability may e.g. be caused by the prolonged integrity of the particle(s) according to the invention, which may be associated with a more rapid gastric emptying of the particle(s), similar to the more rapid gastric emptying observed with pellet formulations, which are believed to pass even the closed pylorus.

Possibly, the polysaccharide component prolongs the integrity of the particle after ingestion as compared to a lipid particle without the polysaccharide component. Prolongation of particle integrity is the prolongation of time during incubation under in vivo or simulated in vivo conditions in which the majority (more than 50%) of particles do not decrease their volume or mass or melt into droplets. Particle integrity may be readily inferred by visual inspection by the naked eye or by means of a microscope or through imaging technology, including microscopic imaging, and subsequent computer-aided image processing. Prolonged integrity of the lipid-containing particle may result in more rapid gastric emptying of the particles and therefore more rapid interaction of particle-derived fatty acids or fatty acid esters with the intestinal mucosa. Prolonged integrity of the lipid-containing particle may also result in the delivery of fatty acids or fatty-acid esters to the more distal parts of the small intestine such as the jejunum or ileum. With regard to particle integrity, it should be understood, that the same considerations typically also apply to any masticated pieces of e.g. larger ingestible particles.

Possibly, the polysaccharide component increases the digestibility of a lipid component of otherwise limited digestibility such as a hard fat such as for instance tristearin. In a published rat feeding study, tristearin (Dynasan® 118, melting range 72-75° C.) was found to provide an energy content of only 3 kcal/g, corresponding to a true digestibility of stearic acid from tristearin of only 0.15 g/g independent from intake. Possibly, the polysaccharide component enhances the particle's surface wetting properties and/or facilitates water and bile acid access and subsequent emulsification and lipase-mediated hydrolysis of the lipid.

In any case, the inventors have found that the oral administration of the particles of the invention to human subjects leads to a sensation of satiety, or increased satiety.

As used herein, an ingestible particle is a particle which is in principle suitable for oral ingestion, or oral administration. A particle which by virtue of its composition, size and morphology would be suitable as a food component or a component of a pharmaceutical composition for oral use is an example of an ingestible particle.

The particles have a sieve diameter in the range from about 0.01 mm to about 10 mm, which means that they, or at least the majority of the particles, would normally pass through a sieve having an aperture or opening size of about 10 mm, but not through a sieve having an aperture or opening size of about 0.01 mm or less. Optionally, the particles may also have a diameter in the range from about 0.05 mm to about 3 mm, or from about 0.1 mm to about 2.5 mm, or from about 0.1 mm to about 2 mm, such as about 0.25±0.20 mm, about 0.5±0.25 mm, about 1.0±0.25 mm, about 1.5±0.25 mm, or about 2.0±0.25 mm, respectively. Within a composition comprising a plurality of particles according to the invention, these particle sizes should be interpreted to characterise the preferred mass median sieve diameters of the ingestible particles.

If the particles are to be swallowed as such, it is also preferred that they have a mass median sieve diameter in the range from about 0.1 mm to about 3 mm. Larger particles with a mass median sieve diameter in the range of up to 10 mm on the other hand may easily be chewed, since the particles are not sticky when in contact with saliva. Also preferred are mass median sieve diameters in the range from about 0.5 mm to about 10 mm, or from about 0.6 mm to about 8 mm, or from about 0.65 mm to about 7 mm, or from about 0.7 mm to about 5 mm or from about 0.75 mm to about 2.5 mm, or from about 1 mm to about 2 mm. In other preferred embodiments, the mass median sieve diameter may be in the range from about 0.1 mm to about 0.4 mm, from about 0.2 mm to about 0.5 mm, or from about 0.2 mm to about 0.4 mm, respectively.

For the avoidance of doubt, these preferred particle sizes are intended as a general teaching and are applicable to all alternative embodiments of the ingestible particles as well as e.g. the "extragranular" components A, B, C, D and/or E, and all uses of the ingestible particles or compositions comprising them.

The water-soluble polysaccharide component is a hydrophilic or amphiphilic material based on glucose or fructose with an average degree of polymerisation from 2 to 100, or from 4 to 80. Preferably, the average degree of polymerisation is from about 5 to about 60. The water-soluble polysaccharide component is capable of dissolving in an aqueous environment. Preferably, the polysaccharide component exhibits a solubility of at least 2 wt.-%, or at least 3 wt.-%, or at least 4 wt.-% and optionally of at least 5 wt.-%, measured in purified water at 25° C.

In a preferred embodiment, the polysaccharide component comprises an essentially non-swelling and essentially non-mucoadhesive polymer; i.e. the polysaccharide component as such essentially does not have, or induce, any pronounced mucoadhesive properties. This provision applies equally to the water-soluble polysaccharide component and to the water-insoluble polysaccharide component.

As used herein, swelling by water, or in an aqueous environment, typically means the volume increase of a solid body caused by an influx, or diffusion process of water accompanied by hydration, i.e. wetting and absorption of moisture. Swelling may e.g. may expressed by the swelling value in percent calculated as $(w_s-w_d)/w_d \times 100$ (with $w_d$=initial weight of dry component and $w_s$=weight of swollen component). For the purposes of this study, swelling, or swelling capacity, is to be understood as the swelling behavior in vivo and should thus be evaluated under conditions mimicking those in vivo; e.g. by placing a fixed amount ($w_d$) of the polysaccharide in excess drinking water of 37° C.±2° C. for 4 hours, before removing excess water with the help of a filter and weighing the weight of swollen component ($w_s$). The term 'non-swelling' as used herein shall refer to a swelling value of not more than 10%, preferably not more than 5%.

Mucoadhesiveness, as used herein, is the capability of adhering to a mucosa, or mucosal membrane. Various conventional methods are available to determine mucoadhesiveness, such as tensile strength measurements, ellipsometry, or rheological measurements (D. Ivarsson et al., Colloids Surf B Biointerfaces, vol. 92, pages 353-359, 2012). Even though these methods may not provide absolute values for mucoadhesiveness as such, they indicate the presence and relative magnitude of mucoadhesiveness of a material.

To determine mucoadhesiveness in the context of the invention, it is preferred that a modified falling liquid film method (described among other methods in Mucoadhesive drug delivery systems, Carvalho F. C. et al., Brazilian Journal of Pharmaceutical Sciences 46 (2010)) is employed. According to the method, the selected mucous membrane (e.g. from pig stomach) is placed in a petri dish together with simulated gastric fluid at a controlled temperature of 37° C. The petri dish is placed on a table undergoing a tilting movement. Both tilting movement and volume of buffer are selected so that small waves of buffer continuously run over the surface of the mucous tissue. In the falling liquid film method, a similar agitation is achieved by pumping buffer over mucosal tissue tilted at a 45° angle. The amount of particles remaining on the mucous membrane after a specified time interval can be quantified by various methods. For instance, particles can be counted, optionally using a magnifying glass or microscope, or they may be collected, dried and measured gravimetrically.

In a preferred embodiment, the particle of the invention comprises a neutral (i.e. non-ionic) polysaccharide that is resistant to digestion in the human small intestine. Examples of suitable non-ionic polysaccharides include, but are not limited to, glucans such as beta glucans; dextrins; fructans such as inulin; *pullulans*; cellulose or hemicellulose. Preferably, the neutral polysaccharide is a non-ionic dietary fibre, e.g. a soluble or an insoluble dietary fibre. Preferably, the neutral, water-soluble polysaccharide is selected from the group consisting of cereal-derived beta glucans such as oat beta glucan or barley beta glucan, inulins and resistant dextrins from starch. The neutral, water-insoluble polysaccharide may be selected, for instance, from the group consisting of cellulose, hemicellulose and long-chain and/or branched beta glucans such as bacteria derived curdlan.

Resistant dextrins are partially hydrolysed starches; i.e. short chain glucose polymers, without sweet taste which are water-soluble and relatively resistant to the hydrolytic action of human digestive enzymes. They can be made for instance from wheat (Nutriose® FB range or Benefiber®) or maize starch (Nutriose® FM range), using a highly controlled process of dextrinisation (heating the starch in the presence of small amounts of food-grade acid), followed by a chromatographic fractionation step. This produces a highly indigestible, water-soluble dextrin, with a high fibre content of about 65-85%, and a more narrow, favourable molecular weight distribution; e.g. approx. 4000 to 6000 Da for Nutriose® 6, or 3500 to 4500 Da for Nutriose® 10 (other dextrins, e.g. one of the starting materials to prepare resistant dextrins, may exhibit broader molecular ranges such as from about 3000 to 10,000 Da). During the dextrinisation step, the starch undergoes a degree of hydrolysis followed by repolymerisation that converts it into fibre and results in a drastically reduced molecular weight and the introduction of new glucoside linkages: in addition to the digestible α-1,4 and α-1,6 glycosidic linkages as commonly found in starches and the digestible maltodextrins, also non-digestible glycosidic bonds such as β-1,2 or β-1,3, are formed in resistant dextrins, which cannot be cleaved by enzymes in the digestive tract. As a result, a portion of the dextrin is not digested in the upper part of the gastro-intestinal tract and is not directly available as such for energy utilisation. Further, some commercial suppliers offer grades with different levels of mono- and di-saccharides (e.g. Nutriose® 10>Nutriose® 6, as available from e.g. Roquette), while the composition of the higher molecular weight oligomers is the same in both grades.

In one embodiment, the water-soluble polysaccharide component comprises a dextrin having a degree of polymerisation from 2 to 100, preferably from 4 to 40, or from 5 to 40, or from 8 to 40, or from 10 to 30 and further preferably from 12 to 25. In one embodiment, the water-soluble polysaccharide component comprises a dextrin having a dextrose equivalent of not higher than 20, preferably a dextrose equivalent of 5 to 15.

In another embodiment, the polysaccharide component is an inulin. Inulins are water-soluble, indigestible polysaccharides, naturally occurring as a storage carbohydrate in many types of plants such as chicory which is most often used for extraction of inulin. Inulins consist of glucose and fructose moieties which are linked by β-(2,1) bonds, which renders them indigestible to the enzymes in human GI-tract and contributes to the functional properties of inulins, such as reduced calorie value, dietary fibre, prebiotic effects and only very mild sweetening. The degree of polymerization (DP) of the inulin may range from 2 to 100. The degree of polymerization (DP) of standard inulin ranges from 2 to 60. In one embodiment, the polysaccharide component comprises an inulin having a degree of polymerisation from 4 to 60, or from 10 to 60, more preferably from 4 to 30, or from 3 to 50 or from 5 to 25.

In a further embodiment, the polysaccharide component is a fructooligosaccharide (FOS); also referred to as oligofructose or oligofructan. Similar to inulin, oligofructose is a naturally occurring storage carbohydrate in plants such as chicory and is based on 3-10 β-glycosidically linked fructose units.

Inulin and oligofructose are commercially available from Raffinerie Tirlemontoise S.A., Brussel as Raftilin® or Raftilose®. Further fructooligosaccharides are commercially available; e.g. Actilight® from Cerestar/Cargill.

In a further embodiment, the water-soluble polysaccharide component is a soluble glucan. Non-limiting exemplary glucans include polydextrose, cyclodextrin, soluble beta-glucans and mixtures thereof. In one advantageous embodiment, the glucan is polydextrose. Polydextrose (also known as E1200) is a water-soluble fibre synthesized from dextrose (glucose), about 10% sorbitol and 1% citric acid; commercially available e.g. as Litesse® from Danisco.

In a further advantageous embodiment, the soluble glucan is a soluble beta-glucan. Beta-glucans (β-glucans) are polysaccharides of D-glucose monomers linked by β-glycosidic bonds, which occur e.g. in the bran of cereal grains. Some forms of beta-glucans such as those derived from oats or other cereals are useful as soluble dietary fibres, since oat is rich in the water-soluble yet indigestible fibre (1,3/1,4) β-glucan. In addition, oat beta glucan (e.g. commercially available as PromOat® from Tate & Lyle) has been shown in clinical trials to lower blood cholesterol and reduce post-prandial glycaemic response.

In a yet further embodiment, the glucan is a cyclodextrin. Cyclodextrins are commercially available from Wacker (Germany); for instance Cavamax®, alpha-cyclodextrin, is available in food-grade qualities.

As mentioned, the water-soluble polysaccharide component in the solid phase described herein may be replaced by a water-insoluble, non-swelling, edible polysaccharide component. Examples of suitable water-insoluble, non-swelling, edible polysaccharide component include cellulose, hemicellulose or long-chain and/or branched beta-glucans like curdlan. Curdlan is an example of a neutral, high-molecular-weight, essentially linear and non-digestible beta-(1,3)D-glucan approved for usage in food products. Unlike the water-soluble cereal derived beta-glucans, curdlan is produced by bacteria such as *Alcaligenes faecalis* and water-insoluble. At body temperature, curdlan forms suspensions; only upon heating the suspensions to temperatures above 80° C., elastic gels are formed.

Optionally, the water soluble polysaccharide component according to the invention comprises more than one polysaccharide as defined herein.

In a preferred embodiment, the particle of the invention comprises not more than 5 wt.-% of mucoadhesive polymer. Optionally, the content of the mucoadhesive polymer in the particle is not more than about 4 wt.-%, or not more than 3 wt.-%, or not more than 2 wt.-%, or not more than 1 wt.-%, respectively. In one embodiment, the particle is free or substantially free of mucoadhesive polymer. As use herein, the term "substantially free" means that the particle contains less than a functional amount of the mucoadhesive polymer, typically less than 1 wt-%, preferably less than 0.1 wt-% or even 0.01 wt-%, and also including zero percent of the mucoadhesive polymer. In yet another embodiment, the particle essentially consists of the water-soluble polysaccharide component and the fatty acid glyceride component as defined herein, and optionally one or more further excipients without mucoadhesive properties, such as sugars, sugar alcohols, vitamins, amino acids, proteins and/or micronutrients.

However, if a minor amount (as described above) of a mucoadhesive material is incorporated into the particle of the invention, such material may be selected from:
(a) poly(carboxylates) such as poly(acrylic acid) (optionally in crosslinked form, e.g. carbomers like Carbopol® or polycarbophils like Noveon® AA-1), poly(methacrylic acid), copolymers of acrylic and methacrylic acid, and poly(hydroxyethyl methacrylic acid), alginic acid or salts thereof, or pectins;
(b) cellulose ethers such as carboxymethylcellulose hydroxyethyl cellulose, hydroxypropyl cellulose (also known as hyprolose), hydroxypropyl methylcellulose (also known as hypromellose), and methylcellulose,
(c) mucoadhesive polysaccharides like chitosan, gellan gum, guar gum, or xanthan gum, and
(d) gum arabic (a mixture of glycoproteins and polysaccharides).

According to the present invention, the fatty acid glyceride component has a melting point or melting range of higher than 37° C. In the context of the present invention, the melting point refers to the fatty acid glyceride component as such, i.e. not in its hydrated state, and it should be understood as the temperature at which the glyceride component melts entirely, without solid residue, at normal pressure. If a glyceride component exhibits a broad melting range, the melting point is understood as the higher limit of the range.

In one embodiment, the fatty acid glyceride component has a melting point from 38° C. to 75° C., in particular from 40° C. to 70° C., or from 40° C. to 65° C. In blends, at least the fatty acid glyceride component and/or at least one of the fatty acid glyceride components has a melting point or melting range of higher than 37° C. In a preferred embodiment, the mass fraction of low-melting constituents (mp below 37° C.) in the fatty acid glyceride component is limited to less than 20%, preferably less than 10%, and more preferably less than 5% or even less than 2%. In case the content of low-melting fractions is higher, the fatty acid glyceride component may potentially be perceived as sticky, or "gluey", upon mastication.

The fatty acid glyceride component is preferably a mono-, di- or triglyceride, and comprises at least one medium or long chain fatty acid residue. In the case of di- and triglycerides, these may have different fatty acid residues per glyceride molecule. The acyl chain of the fatty acid may be saturated or unsaturated.

Optionally, fatty acid glycerides components having a high content of triglycerides are used, e.g. with at least 60 wt.-% triglycerides, or at least 70 wt.-% triglycerides, or at least 80 wt.-% triglycerides, or at least 90 wt.-% triglycerides. Optionally, the glyceride substantially consists of triglyceride(s). Moreover, it is also preferred that the content of the fatty acid triglyceride in the particle is at least 10 wt.-%. Optionally, the content of the fatty acid triglyceride in the particle is at least 20 wt.-%, or at least 30 wt.-%, or at least 40 wt.-%, or at least 50 wt.-%, respectively.

The constituent(s) of the fatty acid glyceride component may represent a native, synthetic or semisynthetic material. In a preferred embodiment, the fatty acid glyceride component is a native material, i.e. obtained from a natural source by extraction, but without chemical modification. For example, a native or natural triglyceride is not hardened or hydrogenated. Irrespective of the source of the constituent(s) of the fatty acid glyceride component, non-hydrogenated constituents are preferred over partially hydrogenated or fully hydrogenated constituents; and fully hydrogenated are again preferred over partially hydrogenated ones due to e.g. the occurrence of trans-fatty acids. Furthermore, "non-trans-esterified" constituents are preferred over "trans-esterified" ones.

A medium chain fatty acid is understood as fatty acid with an acyl residue of 6 to 12 carbon atoms, whereas a long chain fatty acid means a fatty acid with an acyl chain of 13 to 21 carbon atoms. Among the preferred medium chain fatty acids are capric acid and lauric acid, including their esters and salts, in particular their mono-, di- and triglycerides and their sodium, potassium and calcium salts. Examples of preferred long chain fatty acids include myristic acid, palmitic acid, stearic acid, arachidic acid, behenic acid, myristoleic acid, palmitoleic acid, sapienic acid, oleic acid, linoleic acid, and linolenic acid, and the respective salts and glycerides. While the incorporation of polyunsaturated fatty acids such as linoleic acid in the ingestible particles offers a number of health benefits, their amount should be selected with care in order to not render the fatty acid glyceride component sticky or "gluey"; preferably their mass content in the ingestible particles should not surpass 10 wt.-%.

In another embodiment, the fatty acid glyceride component comprises one or more partial glycerides of a medium or long chain fatty acid, in particular monoglycerides of a medium or long chain fatty acid. For example, monolaurin would be suitable for carrying out the invention. As used herein, a monoglyceride such as monolaurin may be incorporated as a substantially pure compound or as a mixture of mono- and diglycerides or even mono-, di- and triglycerides with various fatty acids, but with a high content ("enriched") of a particular monoglyceride compound. For example, a monolaurin grade may be used which comprises at least about 40% (or at least about 50%, or 60% or 70% or 80% or 90%) of the actual monoglyceride of lauric acid.

A preferred fatty acid glyceride component having a melting point or melting range of above 37° C. is fractionated but non-hydrogenated palm stearin or palm kernel stearin. Palm stearin is the solid fraction of palm oil that is produced by partial crystallization at controlled temperature. It is commercially available e.g. as Prifex® 300 from Sime Darby Unimills.

In one specific embodiment, the particle may comprise a combination of a water-soluble polysaccharide component comprising a resistant dextrin derived from wheat or maize starch (such as Nutriose® or Benefiber® or the like) and a fatty acid glyceride component comprising a fractionated but non-hydrogenated palm stearin or palm kernel stearin (such as Prifex® or the like).

It was surprisingly found by the inventors, that the ingestible particles of the invention—and in particular particles comprising mixtures of resistant dextrin(s) and fractionated but non-hydrogenated palm stearin or palm kernel stearin as the fatty acid glyceride component—exhibit a surprisingly pleasant mouthfeel. This is important especially for particles larger than 3 mm, since these typically will not be swallowed as such, but are chewed, or masticated.

The term 'mouthfeel' as used herein covers on the one hand texture properties as defined by tactile perceptions of pressure and contact in the mouth (e.g. fatty, creamy, oily, viscous, sticky, liquid, powdery, sandy, grainy). On the other hand, kinaesthetic perceptions during biting, chewing and swallowing are included (e.g. crunchy, firm, brittle, crumbly, crispy, resilient). Furthermore, geometric properties of a food (e.g. size, form and amount of broken pieces), properties connected with the water content of the food (juicy, dry) as perceivable by tongue and palate are involved in the mouthfeel too; as well as all properties based on temperature perception (hot, cooling) and irritating/painful perceptions of free nerve endings (e.g. spicy, tingling, burning). Commonly, high melting a fatty acid glyceride components do not provide a good mouthfeel in that they cannot melt or noticeably soften at body temperature and are thus mostly perceived as too hard and/or too 'plastic-like', like ingesting a foreign object rather than something edible. The addition of the polysaccharide component as defined herein- and in particular the addition of the resistant dextrins—to the solid phase helps to improve the mouthfeel, e.g. by making the fatty acid glyceride component appear softer and/or smoother, yet crunchy, or crispy, at the same time. Chewability is also improved in that the solid phase appears less 'plastic-like' or brittle. Advantageously, the solid phase does not get sticky or slimy by the addition of the polysaccharide components such as the resistant dextrins, so that it can be chewed, or masticated, easily without e.g. adhering to the gums and/or teeth.

Without wishing to be bound by theory, it is suggested that by adding the polysaccharide component, such as the resistant dextrin, to the ingestible particles, water can be absorbed and/or adsorbed more easily, thereby rendering the mouthfeel of the hard, high-melting fatty acid component softer, less dry, 'plastic-like' or brittle and overall more 'food-like'. In addition, absorbed water may potentially reduce the melting temperature of the fatty acid component just enough to allow for partial melting to occur at the surface layer of the ingestible particles (or masticated pieces thereof) which is likely perceived by the tongue as being more pleasant.

In one of the preferred embodiments, the water-soluble polysaccharide component and of the fatty acid glyceride component make up the majority of the mass of the particle so that the combined content of the water-soluble polysaccharide component and of the fatty acid glyceride component in the particle is at least about 50 wt.-%. Optionally, the combined content of the water-soluble polysaccharide component and of the fatty acid glyceride component in the particle is at least 60 wt.-%, or at least 70 wt.-%, or at least 80 wt.-%, or at least 90 wt.-%, or at least 95 wt.-%, respectively. The particle may also substantially consist of the water-soluble polysaccharide component and the fatty acid glyceride component. The same may apply for the ingestible particles comprising a water-insoluble, non-swelling, edible polysaccharide component.

In one embodiment, the particle further comprises one or more free fatty acids. For example free oleic acid or lauric acid may be part of the lipid component. Other preferred free fatty acids are mixtures of unsaturated fatty acids such as the so-called omega fatty acids or conjugated linoleic acids (CLA), a family of isomers of linoleic acid. Brands of CLAs are marketed as dietary supplements (Tonalin®, BASF, and Clarinol®, Stepan). Examples of omega-3 fatty acids are α-linolenic acid (ALA) (found in plant oils), eicosapentaenoic acid (EPA), and docosahexaenoic acid (DHA) (both commonly found in marine oils). If the fatty acid glyceride component comprises an unsaturated fatty acid, the particle according to the invention may optionally comprise an antioxidant such as vitamin E or a derivative thereof.

It has been surprisingly found by the inventors that particles containing the polysaccharide component as defined herein in intimate mixture with a fatty acid glyceride component as defined herein are capable of exhibiting a prolonged integrity of the particles; the same applies to any masticated pieces of the ingestible particles. Possibly, this contributes to, or is related to, the increased bioavailability of the fatty acid glyceride component(s)—as for instance measured by increased cPDR in a breath test study (see Example 2)—and the improved induction of satiety caused by the particles' administration. Without wishing to be bound by theory, this increase in bioavailability may e.g. be caused by the prolonged integrity of the particle(s) according to the invention which may result in a more rapid gastric emptying of the particle(s).

Typically, the preparation of the intimate mixture means that the fatty acid glyceride component and the polysaccharide component are mixed in such a way that the porosity of the resulting fatty acid glyceride-polysaccharide composition is greatly reduced as compared to the particles formed from the polysaccharide component itself, for instance as formed by roller compaction or agglomeration. This probably contributes to, or is related to, the increased particle integrity of the ingestible particles as described above and/or masticated pieces thereof. Particle porosity may be determined by porosimetry, an analytical technique used to determine various quantifiable aspects of a material's porous nature, such as pore diameter, total pore volume, and surface area. The technique involves the intrusion of a non-wetting liquid at high pressure into a material through the use of a porosimeter.

As already discussed, it is a key feature of the invention that the polysaccharide component is in an intimate mixture with the fatty acid glyceride component, which appears to effect an improved and/or prolonged interaction of the fatty acid glyceride component with target structures in/at the gastrointestinal mucosa. A target structure may, for example, be represented by G-protein coupled receptors (GPCRs) involved in the sensing of intestinal lipids such as GPR120.

In some embodiments, this may also result in an increased bioavailability of the fatty acid glyceride component. In this context, bioavailability should be broadly understood such as to include the availability of e.g. the fatty acid glyceride component, or the biologically active constituents thereof, at a biological target site, such as the gastric or intestinal mucosa, in terms of the extent and/or duration of availability.

To further enhance the beneficial effects of the particle, it is preferred that the weight ratio of the fatty acid glyceride component to the polysaccharide component is in the range from about 0.1 to about 10. In some embodiments, the weight ratio is from about 0.1 to about 5, from about 0.3 to about 3, from about 0.5 to about 2, respectively. Preferred is a weight ratio from about 0.5 to about 5. For the avoidance of doubt, these preferred ratios are intended as a general teaching and are applicable to all alternative embodiments of the composition of the invention with respect to the selection of components A, B, C, D and/or E, and apply to all uses of the compositions.

The inventors have found that the satiety-inducing effect of a free or esterified fatty acid is enhanced if delivered in the form of the particle of the invention, which allows appetite suppression and the prevention and/or treatment of obesity even without pharmacological intervention using a synthetic drug. It is therefore a preferred embodiment that the particle is free of a synthetic drug substance. In other words, the particle may substantially consist of the polysaccharide component and the fatty acid glyceride component, and optionally the components described above and/or other pharmacologically inert excipient(s) such as an inert core.

In fact, it is preferred that not only the ingestible particles but also the entire composition which may further include e.g. one or more of components A, B, C, D or E (as will be described in more detail below) is substantially free of a pharmacologically active ingredient which is not a fatty acid glyceride component.

Optionally, the particle may further contain an amino acid, a protein, a vitamin, a micro-nutrient, or any combinations of these.

As used herein, an amino acid is an organic compound having an amino group and a carboxyl group, mostly in the generic structure of $NH_2$—CHR—COOH wherein R represents the side chain which is specific to each amino acid. Optionally, the carboxylic group is partially or fully neutralised. The amino acid may be provided in its L-form, its D-form or in its racemic form. In a preferred embodiment, the amino acid is a proteogenic amino acid, i.e. an amino acid which is a potential precursor of a protein in that it may be incorporated into a protein during its translation, or biosynthesis. Proteogenic L-amino acids as currently identified are L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, L-selenocysteine, L-pyrrolysine, and N-formyl-L-methionine. In another embodiment, the amino acid is selected from the 20 amino acids which form the genetic code, which group consists of L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

In another preferred embodiment, the amino acid is selected from the group of the so-called essential amino acids which consists of those amino acids which the human organism cannot synthesise, i.e. L-histidine, L-isoleucine, L-leucine, L-lysine, L-methionine, L-phenylalanine, L-threonine, L-tryptophan, and L-valine.

In a further preferred embodiment, the amino acid is selected from the group consisting of L-isoleucine, L-valine, L-tyrosine, L-methionine, L-lysine, L-arginine, L-cysteine, L-phenylalanine, L-glutamate, L-glutamine, L-leucine, and L-tryptophan. From these, the group consisting of L-phenylalanine, L-leucine, L-glutamine, L-glutamate, and L-tryptophan is particularly preferred. In another preferred embodiment, the amino acid is L-tryptophan.

Optionally, the particle comprises two or more amino acids. Such mixture or combination of amino acids should preferably comprise at least one amino acid as described above, i.e. a proteogenic amino acid, or an amino acid from the group of amino acids forming the genetic code, or from the essential amino acids, or the group of amino acids consisting of L-isoleucine, L-valine, L-tyrosine, L-methionine, L-lysine, L-arginine, L-cysteine, L-phenylalanine, L-glutamate, L-glutamine, L-leucine, and L-tryptophan. Particularly preferred particles with mixtures or combinations of amino acids comprise at least one amino acid from the group consisting of L-phenylalanine, L-leucine, L-glutamine, L-glutamate, and L-tryptophan. In particular, L-tryptophan is a preferred constituent of a combination of two or more amino acids.

Also preferred are mixtures or combinations of amino acids in which at least two amino acids are members of one of the preferred groups as previously defined. Moreover, mixtures or combinations of amino acids may be used in the particles of the invention in which essentially all incorporated amino acids are members of one of the preferred groups as previously defined.

As used herein, proteins are macromolecules, consisting of one or more chains of amino acid residues, typically characterized by a specific three-dimensional structure determining the protein's activity, the so-called protein folding. The protein can be native or modified and can be derived from vegetable or animal sources. The term 'proteins' as used herein also includes longer linear chains of amino acid residues with typically more than 20-30 amino acid residues; so-called polypeptides.

If present, the ingestible particles preferably comprise one or more proteins selected from the group of legume proteins, grain proteins, nut proteins, mushroom proteins, and proteins from the seeds of other plants, milk proteins, egg proteins and gelatin. Particularly suitable vegetable proteins include soy protein, rice protein, hemp seed protein, pea protein lupin protein and almond protein.

As used herein, vitamins are organic compounds, or a related set of compounds, acting as vital nutrients required in small amounts, which e.g. humans (or other organisms) typically cannot synthesise in sufficient quantities and which therefore must be taken up with the diet. Their lack typically results in a pathological deficiency condition. The term 'vitamin' is conditional in that it depends on the particular organism; for instance ascorbic acid is a vitamin for humans, while many other animals can synthesise it. Vitamins are organic compounds classified by their biological and chemical activity, not by their structure. Each vitamin refers to a number of vitamers, all having the biological activity of the particular vitamin, convertible to the active form of the vitamin in the body, and grouped together under alphabetized generic descriptors, such as 'vitamin A'. Universally recognised vitamins are preferred for the present invention (related vitamer(s) in brackets):

vitamin A (retinol, retinal, and the carotenoids, including beta carotene, cryptoxanthin, lutein, lycopene, zeaxanthin), vitamin B1 (thiamine), vitamin B2 (riboflavin), vitamin B3 (niacin, niacinamide), vitamin B5 (pantothenic acid), vitamin B6 (pyridoxine, pyridoxamine, pyridoxal), vitamin B7 (biotin), vitamin B8 (ergadenylic acid), vitamin B9 (folic acid, folinic acid), vitamin B12 (cyanocobalamin, hydroxycobalamin, methylcobalamin), vitamin C (ascorbic acid), vitamin D (cholecalciferol (D3), ergocalciferol (D2)), vitamin E (tocopherols, tocotrienols), vitamin K (phylloquinone, menaquinones). The vitamins according to the invention may be provided as semisynthetic and synthetic-source supplements and/or as supplements of natural origin; such as in the form of plant extracts.

As used herein, the term 'micro-nutrients' refers to nutrients required by humans and/or other organisms in small quantities for a variety of their physiological functions, their proper growth and development; including, for instance, dietary micro-minerals or trace elements in amounts generally less than 100 mg/day (as opposed to macro-minerals). The micro-minerals or trace elements include at least boron, bromine, cobalt, chromium, copper, fluoride, iodine, iron, manganese, molybdenum, selenium, and zinc. They may optionally be present in ionised or complexed form or as a salt, an oxide or a chelated salt.

Micro-nutrients also include phytochemicals, such as terpenoids or polyphenolic compounds, organic acids, choline, cholesterol as well as vitamins (i.e. some compounds may qualify for both categories, vitamins and micro-nutrients).

Preferred micro-nutrients according to the invention may be selected from organic acids, such as acetic acid, citric acid, lactic acid, malic acid, and taurine; and trace—or micro-minerals such as salts of boron, bromine, cobalt, chromium, copper, fluoride, iodine, iron, manganese, molybdenum, selenium, or zinc; choline and cholesterol.

These optional components, e.g. the amino acid, the protein, the vitamin and/or the micro-nutrient may be incorporated within the particles of the invention in different ways. For example, hydrophilic compounds such as amino acids, water-soluble vitamins and water-soluble micro-nutrients may be incorporated in admixture with the water-soluble polysaccharide component, whereas lipophilic compounds may be incorporated in admixture with the fatty acid glyceride component.

The particle according to the invention may be in the form of a granule, a pellet, or a minitablet. More preferably, the particle is a granule and/or a pellet. However, it should be noted, that the satiety inducing effect of the particles of the invention usually does not rely on the specific shape of the particle but on the particle's composition.

As used herein, a granule refers to an agglomerated particle which has been prepared from a plurality of smaller, primary particles. Hence, as used herein the term granule(s) does not necessarily imply a specific shape, since the final shape of the granule(s) will be guided by the specific method of preparation. Agglomeration, or granulation, for the purpose of preparing a granule, may involve the use of a dry, wet or melt granulation technique as will be detailed further below.

A pellet, as used herein, is understood as a particle with a relatively spherical or spheroidal shape. If prepared by an agglomeration process, a pellet is a special type of granule. However, pellets (i.e. spherical or spheroidal particles) may also be prepared by other processes than agglomeration. For the avoidance of doubt, the degree of sphericity of a pellet may differ in various technical fields. In the context of the invention, the sphericity of a pellet is in the typical range of pellets used in pharmaceutical formulations for oral use, which often have an aspect ratio of longest space diagonal divided by shortest space diagonal in the range of about 1 to 1.5.

A minitablet, often also referred to as a microtablet, is a unit formed by the compression or compaction of a powder or of granules. Typically, the compression is done on tablet presses using punches.

Minitablets, tablets or capsules comprising the particles of the invention are preferably formulated and processed in such a way that they rapidly disintegrate after oral administration. As used herein, disintegration is understood as a substantial physical change to the minitablet, tablet or capsule morphology, such as the rupture or detachment of the tablet's coating, the dissolution of a capsule or the disintegration of a tablet or minitablet to release particles or pellets or granules of the invention. For the detection of such tablet, minitablet or capsule disintegration behaviour, a microscope may be used. With respect to the apparatus, the hydrodynamic conditions, and the temperature, the method <701> of the United States Pharmacopeia 29 (USP29) may be used, except that water may be used as test medium and that the wire mesh may be adapted with respect to the mesh size or aperture to take the sieve diameter of the tablet, minitablet or capsule into account. When tested according to this method, the minitablets or tablets or capsules comprising particles according to the invention preferably disintegrate within not more than about 15 minutes. More preferably, they disintegrate within about 10 minutes or less. According to another embodiment, they disintegrate within about 8 minutes or less, or within about 5 minutes or less, respectively.

Particles according to the invention may be prepared by a method comprising the steps of (i) preparing an intimate mixture comprising the polysaccharide component and the fatty acid glyceride component and (ii) processing the intimate mixture to obtain ingestible particles of said mixture by (a) extruding the mixture using a screw extruder; (b) spray congealing the mixture, optionally using a jet-break-up technique; (c) melt granulating the mixture; (d) compressing the mixture into minitablets; (e) melt injection of the mixture into a liquid medium; or (f) spray coating of the mixture onto inert cores. The polysaccharide component used in this preparation method may be either a water-soluble polysaccharide component as defined herein or a water-insoluble, non-swelling, edible polysaccharide component as defined herein.

The preparation of the intimate mixture comprising the polysaccharide component and the fatty acid glyceride component may be accomplished by conventional means such as blending or high-shear mixing.

Optionally, the intimate mixture is prepared using the same equipment which is also utilised for the subsequent step in which the particles are formed. For example, for preparing a melt to be used for melt congealing, melt granulation or melt injection, it may not be required to first prepare a dry premix prior to melting the constituents of the melt, but the mixing and melting (or at least partial melting) can be performed simultaneously in one step. In this case, steps (i) and (ii) are performed simultaneously. Therefore, the mixture to be processed according to steps (a) to (f) above should be broadly interpreted to cover any form of combining the materials required for preparing the particles.

In one embodiment, the preparation and/or the processing of the intimate mixture may involve a step of melting the fatty acid glyceride component at least partially and blending in the polysaccharide component.

The wording 'melting at least partially' as used herein means that the melting step does not necessarily have to be performed at temperatures high enough and/or processing times long enough to turn the fatty acid glyceride component into a liquid; a 'partial' melt in the form of a semi-solid, pliable mass may be suitable and in some embodiments even preferred for the invention in terms of e.g. mixing efficiency and/or energy consumption.

It should further be understood, that the step of melting the fatty acid component and the step of blending in the polysaccharide component may occur simultaneously (e.g. a powder blend of the two components being stirred while gradually heated) or in succession (i.e. preparing the melt or partial melt first and only then blending in the polysaccharide component).

In one embodiment, the mixture is extruded using a screw extruder. Optionally, a twin-screw extruder is used for carrying out the extrusion step. The extruder should have a screen with an aperture that is useful for producing an extrudate with appropriate diameter, such as 0.5 mm or 1.0 mm, as commonly used for the preparation of pellets. Of course, larger aperture diameters are feasible, too, for instance when aiming for larger granules of e.g. up to 3 mm. The screw speed may be selected in consideration of the capability of the extruder and on the processability of the mixture. For example, it may be useful to select a screw speed in the range from about 20 rpm to about 100 rpm.

Preferably, the extrusion step is carried out without the use of a solvent and at a relatively low temperature, such as below about 45° C., or below about 40° C., or below about 35° C., or below about 30° C., e.g. at room temperature. It is also preferred that the extrusion step is carried out at a temperature which is lower than the lower limit of the melting point of the fatty acid glyceride component, e.g. 20° C. below the melting temperature. This prevents leakage from the extruder as well as improving the mixing efficiency.

In one embodiment, the ingredients used for preparing the particles by extrusion are mixed or blended before they are fed to the extruder. Alternatively, the ingredients may be mixed using the same equipment which is utilised for the extrusion step. Thus, it is also preferred that the ingredients used for preparing extruded particles are provided to the extruder by co-feeding, using appropriate feeding equipment, and optionally recycled within the extruder (e.g. via internal bypass-loops) until a uniform, intimate mixture is obtained which is ready for subsequent extrusion.

Subsequent to the extrusion step, the extrudate may be spheronised in order to obtain approximately spherical particles. For this purpose, any conventional spheroniser may be used. The temperature of the spheroniser jacket should preferably be set to be lower than the lower limit of the melting range of the lowest-melting constituent of the mixture. The speed of the spheronisation plates may be set between about 200 rpm and about 2,000 rpm, such as about 500 rpm to about 1,500 rpm. Subsequent sieving may be performed in order to select an optimal particle size of the product.

In a particular embodiment, the particles are prepared from the mixture by spray congealing. This process may also be referred to as spray chilling or spray cooling. In this process, a liquid melt is atomised into a spray of fine droplets of approximately spherical shape inside a spray cooling chamber. Here, the droplets meet a stream of air or gas which is sufficiently cold to solidify the droplets. The air or gas stream may have a co-current, mix-current or counter-current direction of flow.

To improve the formation of droplets of appropriate size and shape, a heatable rotary spray nozzle or a fountain nozzle may be used. In the context of the invention, a high speed rotary nozzle is one of the preferred nozzle types for preparing the particles.

Optionally, the uniformity of the atomised droplets may be further enhanced by using a jet break-up technique, such as electrostatic droplet generation, jet-cutting, jet excitation or flow focusing. In general, jet break-up refers to the disintegration of a liquid/gas jet due to forces acting on the jet.

In electrostatic droplet formation processes, a nozzle equipped with an electrode is used which applies an electrical charge to the melt spray. In jet cutting, the spray is directed through a cutter similar to e.g. a rotary disc with apertures of defined size. Jet excitation means the excitation of the melt spray by ultrasonic waves, causing vibration and facilitating the separation of droplets.

Flow focusing results from combining hydrodynamic forces with a specific geometry, which may be achieved by using a pressure chamber pressurised with a continuous focusing fluid supply. Inside, a focused fluid is injected through a capillary feed tube whose extremity opens up in front of a small orifice linking the chamber with the exterior ambient. The focusing fluid stream moulds the fluid meniscus into a cusp giving rise to a microjet exiting the chamber through the orifice. Capillary instability breaks up the stationary jet into homogeneous droplets.

In another specific embodiment, the particles are prepared by injecting the melted mixture into a liquid. The liquid may be cooled to a temperature below room temperature, or preferably to substantially below the lower limit of the melting range of the lowest-melting constituent of the lipid component. The liquid should be selected taking the composition of the mixture into consideration, but also with an eye on safety and physiological tolerability. In many cases, ethanol is a suitable liquid.

In another embodiment, the particles may be formed by melt agglomeration, or melt granulation. In the context of the invention, agglomeration and granulation may be used interchangeably. For this purpose, the constituents of the mixture are mixed or blended and agglomerated, or granulated, in a suitable type of equipment, such as a heatable granulator, a high-shear mixer/granulator or a fluid bed granulator. Depending on the type of equipment, the granulation may be carried out by heating the mixture to a temperature at which at least one of its constituents softens or melts, under continuous stirring or mixing. In a conventional granulator, this may lead to larger agglomerates which are then passed through a sieve to obtain the desired particle size. If fluid bed equipment is used, the complete mixture may be fluidised and heated carefully up to the melting temperature of the lowest-melting constituent. Alternatively, the lowest-melting constituent may be melted and sprayed onto the fluidised powder mixture comprising the remaining constituents.

Optionally, the melt granules may be further processed and compressed into minitablets. For this purpose, it is preferred that the granules are first blended with one or more tablet fillers/binders to enhance the plasticity of the mixture. Moreover, conventional excipients to improve the flow of the granules and reduce their tackiness may also be added before compression. Tableting may be carried out using any conventional pharmaceutical tablet press, such as an eccentric press or a rotary press. Optionally, the press may be equipped with multi-punch tooling so that each compression yields a plurality of minitablets. Punches for very small tablet diameters are preferred for particles intended to be swallowed as such, such as between about 1 mm and about 3 mm, such as about 1.5 mm. For larger particles which are intended to be chewed, larger tablet diameters may be used, such as in the range from about 1 mm to about 10 mm.

Alternatively and depending the mixture's flow properties, the mixture of fatty acid glyceride component and polysaccharide component may also be compressed into minitablets as such; i.e. without a preceding melt granulation step.

In a further embodiment, the particles are prepared by spray coating the mixture comprising the fatty acid glyceride component and the polysaccharide component onto inert cores. As used herein, an inert core is a particle from a physiologically acceptable material which itself does not substantially contribute to the physiological effect of the particles of the invention, i.e. the induction of satiety. Examples of suitable cores include crystals of appropriate size and shape, such as sugar (sucrose) crystals. In one of the preferred embodiments, spherical beads or non-pareils made from sugar, starch, cellulose, in particular microcrystalline cellulose (e.g. Cellets®) are spray coated with the mixture.

The spray coating of the inert cores may, for example, be performed in a fluid bed apparatus. The mixture of the fatty acid glyceride component and the polysaccharide component may be melted and sprayed onto the fluidised core particles. Optional components such as the above mentioned amino acid(s), protein(s), vitamin(s), micro-nutrient(s) or the like which are intended to be incorporated into the ingestible particles (rather than used as extragranular components) may also be added to this mixture. Alternatively, an aqueous or organic dispersion (or suspension, which is understood as a sub-type of a dispersion) of the mixture is sprayed onto the fluidised cores in such a way that the water or solvent evaporates and the mixture of the fatty acid glyceride component and the polysaccharide component forms a coating on the inert core particles.

As in all other processes mentioned above, a subsequent step of classifying the resulting particles using a sieve in order to obtain a more uniform particle size distribution may be useful. Where necessary or useful, the particles may be dried at 25° C. under vacuum prior to classifying them.

According to a further aspect of the invention, an ingestible particle is provided which is obtainable by the method(s) as described above.

In an alternative aspect of the invention, the water-soluble polysaccharide component in any of the preparation processes described above may be replaced by a water-insoluble, non-swelling, edible polysaccharide component, like e.g. cellulose, hemicellulose or long-chain and/or branched beta-glucans like curdlan, such as to obtain an ingestible particle having a sieve diameter in the range from 0.01 mm to 10 mm and comprising an intimate mixture of (a) at least 10 wt.-% of a water-insoluble, non-swelling, edible polysaccharide component, and (b) at least 10 wt.-% of a fatty acid glyceride component having a melting point of higher than 37° C., wherein the particle comprises not more than 5 wt.-% of mucoadhesive polymer, and/or wherein the combined content of the water-insoluble, non-swelling, edible polysaccharide component and of the fatty acid glyceride component in the particle is at least 80 wt.-%.

In a further aspect, the invention provides a solid composition for oral administration comprising a plurality of the particles as described above, or which has been prepared from a plurality of the particles, such as by compressing the particles into tablets. If not compressed into tablets, the particles may in principle be filled into capsules, sachets, stick packs, or containers (e.g. bottles or drink vials of glass or other materials). In one of the preferred embodiments, the particles, or granules, are filled into sachets, stick packs, or containers in such a way that a single dose is accommodated in one primary package.

Optionally, the composition may comprise the particles along with one or more further inactive ingredients, such as e.g. one or more colouring agents, stabilising agents, wetting agents, bulking agents, suspending agents, pH-modifiers, and/or flow-regulating agents.

Further optionally, the compositions may comprise the ingestible particles together with one or more additional "extragranular" components selected from components A to E, as will be detailed below.

In one embodiment, one or more components selected from A to E are provided "extragranular" to the ingestible particles but in the same dosage form and/or primary packaging; e.g. in form of mixtures of the ingestible particles and powders and/or granulates of any one of the optional components A to E. Said mixtures may be compressed to tablets or filled into capsules, sachets, stick packs, vials, bottles, or containers. In a specific embodiment, a powder, a powder blend and/or a granulate of any one of the components A to E may be provided together with a plurality of the ingestible particles in one common stick pack or bottle.

Alternatively, the component(s) selected from A to E may also be provided in separate dosage forms and/or primary packagings, e.g. in the form of a kit; i.e. in separate primary packagings but distributed, or sold, in combination.

The decision on how to add any one of the components A to E to the pharmaceutical composition—e.g. whether in the same pharmaceutical composition as the particles or a separate one—is made independently for each component and may be guided e.g. by weight or stability concerns as well as processability and/or dispersibility considerations.

Component A

Component A comprises a native or modified protein. Preferably, component A comprises one or more proteins selected from vegetable protein and/or animal protein. The vegetable protein may be a legume protein, grain protein, nut protein, mushroom protein, and protein from the seeds of other plants, and the animal protein may, for example, be selected from milk protein, egg protein, and gelatin. Particularly suitable vegetable proteins include soy protein, rice protein, hemp seed protein, pea protein lupin protein and almond protein. Suitable milk proteins include in particular casein and whey protein. Suitable gelatins include gelatin from fish, cattle, pigs, or chicken.

In one embodiment, component A essentially consists of protein powder or a blend of two or more proteins. Alternatively, component A may comprise the protein or protein blend in granulated form, optionally along with one or more other substituents, such as a granulation aid.

In one embodiment, the composition of the invention comprises at least a plurality of ingestible particles as defined above and component A. In particular if the product is also used to substitute a meal, partially or entirely, it is preferred that component A is present. In this case, the amount of component A in the composition may be up to about 90 wt.-%, such as from about 5 wt.-% to about 75 wt.-%, or from about 8 wt.-% to about 60 wt.-%, or from about 10 wt.-% to about 50 wt.-%. In absolute terms, the amount of component A is preferably selected such that a single dose of the composition comprises from about 3 g to about 50 g of protein, such as from about 5 g to about 30 g of protein, or from about 10 g to about 25 g of protein, respectively.

The ratio of the ingestible particles to component A may optionally be in the range from about 1:10 to about 5:1, or from about 1:5 to 2:1, respectively. The ratio of the first lipid material in the ingestible particles to the protein in component A may optionally be in the range from about 1:20 to about 3:1, such as from about 1:10 to about 1:1.

Component B

Component B preferably comprises one or more dietary fibres selected from soluble and/or insoluble dietary fibres. The soluble dietary fibre is preferably a prebiotic or natural gum; and the insoluble fibre is preferably a cellulose, lichenin, chitin, hemicellulose, or lignin.

As used herein, a prebiotic is a compound or material that supports the growth of microorganisms that are hosted by a human and that are beneficial to the host. In particular, a compound or material that is a substrate for the gut microbiome of a human is an example of a prebiotic. Many but no all currently known prebiotics are fibres.

Suitable prebiotic fibres include for example resistant dextrins, inulin, galacto-oligosaccharides, mannan oligosaccharides, and gum arabic. Optionally, component B may comprise the prebiotic fibre in the form of a plant extract which is rich in such fibre, such as extracts from chicory root, asparagus, leek, Jerusalem artichoke, dandelion, garlic, garlic, onion, wheat bran, beans, oats, barley, or banana.

As used herein, a natural gum is a native or modified soluble polysaccharide, or polysaccharide-containing polymer, that substantially increases the viscosity when dissolved in an aqueous medium even at relatively low concentrations. Hence, soluble fibres may also be referred to as viscous fibres. The natural gum may be selected from the group of natural gums representing largely uncharged compounds, or from the group of charged gums, or polyelectrolytes.

Suitable uncharged natural gums may be derived from bacteria, such as xanthan gum, or from botanical sources, such as *Psyllium* seed husks, glucomannan, guar gum, beta-glucans such as oat or barley beta-glucans, locust bean gum, chicle gum, mastic gum, tara gum, spruce gum or dammar gum. Suitable natural polyelectrolyte gums include for example gums from seaweeds, such as agar, alginic acids and alginates, carrageenan; or charged gums from bacteria, such as gellan gum; or from other botanical sources such as gum arabic, gum ghatti, gum tragacanth, pectin, or Karaya gum.

An insoluble fibre is understood as a fibre which is substantially insoluble in water at physiological pH and body temperature. Suitable insoluble fibres include non-starch polysaccharides such as cellulose, lichenin, chitin, hemicellulose, or lignin. Optionally, component B comprises such insoluble fibres in the form of a plant material or plant extract, such as wheat bran, corn bran, or fibre-enriched vegetable or fruit powders.

Component B may also comprise a mixture of different fibres, whether from the same or different categories.

If present in the combination product, component B may be incorporated at any suitable amount, and preferably at an amount of up to about 50 g per single dose of the combination product. Also preferred are amounts from about 0.5 g to about 40 g, or from about 1 g to about 30 g, or from about 2 g to about 25 g, respectively.

Component C

Component C comprises a vitamin, a micro-nutrient such as one or more micro-minerals, organic acids, choline, cholesterol, and/or a further dietary element (also called mineral nutrients). The definitions of vitamins and micro-nutrients as provided above equally apply to component C. The selection of the number, type and/or combination of the one or more vitamin and/or micro-nutrients in component C may be identical to that of the vitamin and/or micro-nutrients optionally employed inside the ingestible particles as described above. However, this is not a requirement; i.e. the ingestible particles may also contain different vitamins and/or micro-nutrients than component C.

A dietary element, often also referred to as an essential element, dietary mineral or mineral nutrient, is a chemical element that is physiologically required by the human body. Dietary elements are sometimes classified in various groups. For example, one group consist of hydrogen, carbon, nitrogen and oxygen, and is considered the basis of life and the quantitative basis of most organic compounds that play a role in human physiology. Another group which consists of sodium, potassium, magnesium, calcium, phosphorus, sulphur, and chlorine is often termed the quantitative elements or macro-minerals, as these elements are physiologically required in substantial amounts. The remaining elements are referred to as micro-minerals (see above under micro-nutrients), trace elements, or essential trace elements, as the amount that is physiologically required is very small.

Preferably component C comprises one or more of the following:

- a vitamin selected from retinol, retinal, beta carotene, thiamine, cyanocobalamine, hydroxycyanocobalamine, methylcobalamine, riboflavin, niacin, niacinamide, pantothenic acid, pyridoxine, pyridoxamine, pyridoxal, biotin, folic acid, folinic acid, ascorbic acid, cholecalciferol, ergocalciferol, tocopherol, tocotrienol, phylloquinone, and menaquinone;
- a micro-mineral selected from boron, bromine, chromium, cobalt, copper, fluoride, iodine, iron, manganese, molybdenum, selenium and zinc (optionally in ionised or complexed form or as a salt, an oxide or a chelated salt);
- an organic acid such as acetic acid, citric acid, lactic acid, malic acid, or taurine;
- choline;
- cholesterol; and/or
- a further dietary element such as a macro-mineral selected from calcium, chlorine, magnesium, phosphorous, potassium, sodium and sulphur (optionally in ionised or complexed form or as a salt, an oxide or a chelated salt).

For micro-nutrients, vitamins and dietary elements, recommendations have been established with respect to the daily intake level that is considered sufficient, adequate and/or acceptable for an average healthy individual by various national and international agencies. For example, the Institute of Medicine of the National Academies of the United States has published a system of nutritional recommendations referred to as the Dietary Reference Intake (DRI), which includes amongst others the Estimated Average Requirement (EAR), expected to meet the nutritional needs of 50% of a specific target group; the Recommended Dietary Allowance (RDA), which is the daily nutrient intake that is considered sufficient for the vast majority (at least 97.5%) of healthy individuals in a specific sex and age group; and the Tolerable Upper Intake Levels (UL), reflecting a maximum daily intake level that appears to cause no harm. The currently recommended EAR, RDA and UL values for micro-nutrients, vitamins and dietary elements are listed in the table below.

| Nutrient | EAR | RDA | UL |
|---|---|---|---|
| Calcium | 800 mg | 1000 mg | 2500 mg |
| Chloride | NE | 2300 mg | 3600 mg |
| Chromium | NE | 35 µg | ND |
| Copper | 700 µg | 900 µg | 10000 µg |
| Fluoride | NE | 4 mg | 10 mg |
| Iodine | 95 µg | 150 µg | 1100 µg |
| Iron | 6 mg | 8 mg | 45 mg |
| Magnesium | 330 mg | 400 mg | 350 mg |
| Manganese | NE | 2.3 mg | 11 mg |
| Molybdenum | 34 µg | 45 µg | 2000 µg |
| Phosphorus | 580 mg | 700 mg | 4000 mg |
| Potassium | NE | 4700 mg | ND |
| Selenium | 45 µg | 55 µg | 400 µg |
| Sodium | NE | 1500 mg | 2300 mg |
| Vitamin A | 625 µg | 900 µg | 3000 µg |
| Vitamin B1 | 1.0 mg | 1.2 mg | ND |
| Vitamin B12 | 2.0 µg | 2.4 µg | ND |
| Vitamin B2 | 1.1 mg | 1.3 mg | ND |
| Vitamin B3 | 12 mg | 16 mg | 35 mg |
| Vitamin B5 | NE | 5 mg | ND |
| Vitamin B6 | 1.1 mg | 1.3 mg | 100 mg |
| Vitamin B7 | NE | 30 µg | ND |
| Vitamin B9 | 320 µg | 400 µg | 1000 µg |
| Vitamin C | 75 mg | 90 mg | 2000 mg |
| Vitamin D | 10 µg | 15 µg | 100 µg |
| Vitamin E | 12 mg | 15 mg | 1000 mg |
| Vitamin K | NE | 120 µg | ND |
| Zinc | 9.4 mg | 11 mg | 40 mg |

Preferably, the amount of a micro-nutrient, vitamin or dietary element in component C is at least about 10% of the RDA of that nutrient, and more preferably at least about 20% of the RDA. Also preferred are amounts representing from about 30% to about 100% of the RDA. Further preferred is a maximum amount corresponding to the UL for the respective nutrient.

Component D

Component D comprises at least one amino acid, optionally in the form of a powder, a powder blend and/or a granulate. The definitions of amino acid(s) optionally comprised inside the ingestible particles as provided above equally apply to component D. The selection of the number, type and/or combination of the one or more amino acids in component D may be identical to that of the amino acid(s) optionally employed inside the ingestible particles as described above. However, this is not a requirement; i.e. the ingestible particles may also contain different amino acid(s) than component D.

Component E

Component E comprises one or more substance(s) for improved flavour, including but not limited to sweetening agents (such as sugars, sugar alcohols, *stevia*/steviosides etc.), bitterness reducing agents or flavouring agents such as natural, semisynthetic or synthetic aroma; plant extracts or powdered plant parts.

Flavouring agents for the purpose of the invention include, but are not limited to synthetic flavour oils and flavouring aromatics and/or natural oils, extracts from plants, leaves, flowers, and fruits, and mixtures of two or more thereof. These may include cinnamon oil, oil of wintergreen, peppermint oils, clove oil, bay oil, anise oil, *eucalyptus*, thyme oil, cedar leaf oil, oil of nutmeg, oil of sage, oils of citrus fruits (for example lemon and orange), oil of bitter almonds and *cassia* oil, vanilla, chocolate, mocha, coffee, ice cream, citrus (including lemon, orange, grape, lime, and grapefruit), apple, pear, peach, mango, strawberry, raspberry, cherry, plum, pineapple, and apricot. The amount of the at least one flavouring agents may depend on a number of factors, including the organoleptic effect desired.

Other Components

The composition may further comprise one or more additional components that may further contribute to its dietary effectiveness or health benefits; for example, non-fibrous prebiotics or omega fatty acid compounds. Further suitable additional components are γ-polyglutamic acid (γ-PGA), seaweed extract, isoflavones, green coffee extract, melon extract, carotenoids, docosahexaenoic acid, fish and krill oil, eicosapentaenoic acid, CoQ10, resveratrol, vegetable and fruit oils, caffeine, ephedra, *capsicum*, ginger, pyruvate, EGCS, taurine, polyphenols, herbal extracts; e. g. chamomile, lemon balm, passion flower, hops, valerian, theanine, lutein esters, lycopene, glucose, palatinose, taurine, ribose, guarana, glucuronolactone, citicoline, yeast beta-glucan, barley beta-glucan, oat beta-glucan, probiotics, plant sterols, tomato extract, chondroitin sulfate, collagen, biotin, electrolytes, conjugated linoleic acid. Some of these components, such as fruit oils, may also be employed for their taste.

Other optional components or constituents may be present in the composition as well as the constituents thereof, such as a colouring agent, a stabilising agent, a wetting agent, a bulking agent, a suspending agent, a pH-modifying agent, and/or a flow-regulating agent.

Suitable colouring agents for the purpose of the invention include, but are not limited to, titanium dioxide and dyes suitable for food such as those known as FD&C dyes and natural colouring agents such as grape skin extract, beet red powder, beta-carotene, annatto, carmine, turmeric, chlorophyll, and pepper.

As mentioned, the composition of the invention comprises the ingestible particles as defined above and optionally one or more of components A, B, C, D or E. The decision on how much of any one of the components A to E is to be added to the composition is made independently for each component. One of the specific benefits of the composition is that is can easily be adapted to the needs of an individual user or patient. An individual in need of e.g. preventing, controlling or reducing obesity or overweight will always benefit from the satiety-inducing effect of the ingestible particles, but at the same time may have different requirements with respect to the other components. For example, a person who wishes to replace a major meal, partially or entirely, with a single dose of the composition on a regular basis, e.g. once a day for a certain period of time, may be interested in ensuring that such substitution will not lead to a lack of essential nutrient intake, such as the intake of protein, vitamins and dietary elements. If the replaced major meal is a protein-rich meal, the composition administered to replace it, partially or entirely, may also be enriched with protein, i.e. comprise component A, in particular if the other meals that are not replaced contain a low amount of protein. On the other hand, if the replaced meal is a light meal, a carbohydrate-rich meal or a snack, and the individual's regular intake of protein is not substantially affected by the meal replacement plan, then it may be more useful to incorporate component C in the composition. If the individual's change in diet tends to result in constipation, or if the health status of the individual indicates a need for—or potential benefit of—additional fibre intake, the composition may be designed to include component B.

The presentation and oral administration of the particles and/or composition comprising or being prepared from them in the form of, or using, sachets, stick packs or containers (e.g. bottles or drink vials) is also useful as it is preferred that a relatively large amount of the composition is administered as a single dose. In one of the preferred embodiments, a single dose unit or package comprises at least about 2 g of the composition, or at least about 3 g thereof. In another embodiment, a single dose unit or package comprises from about 3 g to about 20 g of the composition. In further embodiments, the amount comprised in a single dose is from about 4 g to about 15 g of the composition, or from about 5 g to about 12 g, or from about 5 g to about 10 g, respectively. The amount of the fatty acid glyceride component in the composition is at least 1 g, preferably at least 2 g. In a specific embodiment, a single dose unit or package comprises from about 3 g to about 20 g of the composition and the amount of the fatty acid glyceride component in the composition is preferably at least 2 g.

Where the composition comprises further constituents, such as components A to E, the weight of a single dose will increase correspondingly of course. For instance, the amount of the composition representing a single dose may then be at least about 30 g, or at least about 40 g, or at least about 50 g, respectively; for example in the range from about 30 g to about 150 g, or from about 40 g to about 120 g, or from about 50 to about 100 g, respectively.

It should be understood that these weights refer to the single dose unit or package as provided, or sold, to the consumer; for instance excluding the weight of any liquids which are not present in the single dose unit or package during shipping, storage and sale but which may be added directly prior to actual ingestion by the user, or consumer (like water, milk or juice being added to a single dose of particles in a bottle or drink vial package to form a drinkable suspension).

It should further be understood, that the provision of single dose units or packages and their weights is not intended to exclude the option of multiple dose units or packages. The oral composition may also be provided in larger packages containing multiple doses together with instructions on obtaining a single dose; for instance a 350 g package containing a blend of any of components A to E with the particles of the invention with a serving suggestion printed on the side of the package, such as 'Single serving about 70 g+200 mL added water'.

It is also preferred that the composition exhibits a high content of the particles of the invention, such as at least about 20 wt.-%, or at least about 30 wt.-%, such as from about 20 wt.-% to 100 wt.-%, or from about 30 wt.-% to about 90 wt.-%.

For the purpose of administration, the composition may be suspended in a liquid or semisolid vehicle. I.e. in a further aspect, the invention provides a liquid or semi-solid composition obtainable by dispersing the solid composition and/or the pharmaceutical combination product as defined above in an ingestible liquid. The liquid may simply be water or fruit juice or a dairy beverage such as milk or any other, preferably non-carbonated, ingestible liquid, or mixtures thereof. As used herein, the term milk comprises milk-varieties obtained from animals (e.g. cow, goat or sheep milk) as well as milk varieties of vegetable/plant origin (e.g. soy, rice or nut based milks). The liquid(s) may optionally be provided together with the composition within a kit; e.g. both in separate primary packagings but distributed, or sold, in combination, such that the consumer, or user, himself/herself adds it to the solid phase directly prior to ingestion. This has the advantage that the nature and amount of liquid are controlled and the administration is more reproducible. Alternatively, the ingestible liquid may be provided in the same primary packaging as the ingestible particles, e.g. a drink vial or bottle, in the form of a 'ready-to-use' drink suspension, which does not require reconstitution by the consumer, or user, prior to ingestion. The reconstituted or 'ready-to-use' drink suspensions may have, for example, a volume in the range from about 30 mL to about 300 mL, or from about 40 mL to about 250 mL or from about 50 mL to about 200 mL. In case additional "extragranular" components, such as components A to E, are comprised in the composition, the amount of liquid used for reconstitution may be larger, such as from about 50 mL to about 500 mL.

In a preferred embodiment, the composition of the invention is administered as a suspension drink. It was found that the suspension drink of the invention is useful for administering large amounts, such as 1 g or more, and more typically at least 5 g, such as from about 10 g to about 100 g, of the composition while exhibiting good drinkability and mouth feel. Drinkability of such a suspension drink according to the invention may be assessed by methods used to determine the flowability of wet granular materials. In particular, dynamic measurements of the angle of repose may be taken using a rotating drum apparatus where the whole drum or its bottom and top are transparent or semi-transparent. Such apparatus are commercially available for instance from Mercury Scientific, USA (Revolution Powder Analyzer) and APTIS, Belgium (GranuDruM powder rheometer). In a suitable experimental set up for dynamic measurements of angle of repose of wet granular material comprising aqueous liquid, the drum is preferably made of PTFE (Teflon®) or coated with PTFE or similar anti-adhesive material, and is filled to half of its volume with a suspension of powder or particles. After placing the drum's top and bottom along a horizontal axis, and repeated tapping for even distribution of the drum's contents, the suspension forms a horizontal meniscus of an angle of zero. This may be visually observed and measured by standard methods of angle measurements. Rotating the drum along this horizontal axis may displace the meniscus of the powder suspension to a certain angle before the meniscus of the suspension repositions itself to an angle of almost zero. The displacement of the meniscus from the horizontal may be repeated several times, and a mean value of the dynamic angle of repose may be calculated.

In one embodiment, the suspension drink comprises a plurality of the particles of the invention and at least one aqueous liquid, and the sum of the volume fractions of the particles and the at least one aqueous liquid makes 100 vol-%. Accordingly, the present invention provides a suspension drink, comprising 50 to 75 vol-% of particles according to the invention; and 25 to 50 vol-% of at least one aqueous liquid; wherein the volume fractions are based on the total volume of the suspension drink. Preferably, the dynamic angle of repose of the suspension drink is less than about 30°.

In a further preferred embodiment, the amounts of particles and liquid are selected such that a densely packed suspension drink is obtained by matching the filling height of the particles settled in a suitably sized container with the filling height of the aqueous liquid in the same container comprising the settled particles. In other words, the amount of the liquid is chosen in such manner that the meniscus of the liquid is roughly at the position of the upper limit of the settled particles.

The at least one aqueous liquid further may comprise alcohol, flavouring compounds, colouring compounds, preservatives, viscosity enhancers, health ingredients or mixtures of two or more thereof. Suitable flavouring compounds are citric acid, malic acid, phosphoric acid, tartaric acid, natural and synthetic aroma, sweeteners, for example monosaccharides, disaccharides, polyhydric alcohols; including arabitol, erythritol, glycerol, isomalt, lactitol, maltitol, mannitol, sorbitol or xylitol; or sugar substitutes, including cyclamate, saccharine, *stevia*, sucralose and/or aspartame. Further suitable flavouring compounds are juices of fruits and/or vegetables. Colouring compounds suitable for the aqueous liquid are for example Allura Red AC, Anthocyanine, azorubine, betanin, Brilliant Blue FCF, carotene, Quinoline Yellow WS, Ponceau 4R, Green S, Patent Blue V and tartrazine, either as such or in the form of the corresponding aluminium lakes. Suitable preservatives are vitamins A, E or C, retinyl palmitate, cysteine, methionine, citric acid, sodium citrate, used in amounts of 0.001 to 0.1% by weight based on the liquid.

The amount of the fatty acid glyceride component, which is a key ingredient of the composition, should preferably be at least about 1 g per single dose unit or package. In another embodiment, a single dose unit comprises at least about 2 g of the fatty acid glyceride component, such as about 3 g or about 4 g. In a further preferred embodiment, the content of the fatty acid glyceride component per single dose is at least about 5 g.

If present, the amount of the amino acid (or of the total amino acids, if a mixture or combination of amino acids is used) may be about 0.05 g or more per single dose unit or package. In another embodiment, a single dose unit comprises at least about 0.1 g, or at least about 0.2 g, or at least about 0.5 g of amino acid(s), respectively. In further embodiments, the content of the amino acid(s) per single dose unit is from 0.5 g to about 5 g, or from 0.5 g to about 3 g.

In one of the embodiments, the components of the particles are selected such that the dynamic angle of repose of a suspension prepared from suspending the composition in water at a weight ratio of 1 is less than 30°.

As mentioned, the particles and the compositions of the invention may be used for the suppression of appetite, in particular in human subjects, and for the induction of satiety. This is equally valid for both the particles with the water-soluble polysaccharide component as defined herein and the particles with the water-insoluble, non-swelling, edible polysaccharide component as defined herein. Thus, the invention provides a method of inducing satiety in a subject, wherein the method comprises a step of orally administering a composition comprising an effective amount of a first agent capable of inducing satiety, and a second agent capable of augmenting the satiety-inducing effect of the first agent, and wherein the first and the second agent are optionally selected as described above. Without wishing to be bound by theory, it is currently believed by the inventors that the appetite suppressing effect is at least in part based on the fatty acid compound comprised in the fatty acid glyceride component, which upon ingestion interacts with physiological targets located at/in the mucosa of the gastrointestinal tract, such as in the stomach and/or duodenum, thereby activating one or more signalling cascades which eventually produce a perception of satiety or a reduction of appetite or hunger. Possibly, one of the targets at which the one or more fatty acid(s) act are the ghrelin cells (or ghrelin receptors), large numbers of which are located in the stomach and the duodenum.

If present, amino acid(s) may further contribute to the appetite suppressing effect, which may be due to a stimulation of chemosensors in the proximal gastrointestinal tract by which in turn the CCK and glucagon secretion is triggered.

The polysaccharide component was found by the inventors to enhance the effect of the lipid which may possibly due to the prolonged integrity of the particles and/or masticated pieces thereof, allowing for an increased interaction of the fatty acid(s) of the glyceride with the target structure and resulting in an increased bioavailability of the fatty acid glyceride component(s), as for instance measured by increased cPDR in a breath test study (see Example 2). Of course, other properties of the particles may also effect or contribute to the prolonged integrity of the particles and/or masticated pieces thereof and the increased bioavailability of the fatty acid glyceride component(s), such as the selected particle size or the low density resulting from the high lipid content. Without wishing to be bound by theory, the increase in bioavailability may e.g. be caused by the prolonged integrity of the particle(s) according to the invention, which may be associated with a more rapid gastric emptying of the particle(s) and/or masticated pieces thereof.

In any case, the inventors found that the oral administration of the particles to volunteers induced satiety with the consequence that the subjects experienced suppressed appetite and showed a reduced food intake during the meal following the administration of a composition comprising the particles as described herein. This effect was consistent with animal data showing the composition leads to a weight loss, or weight reduction, of the test animals.

According to a related aspect, the invention provides a method of treating or preventing overweight, obesity, or a disease or condition associated with overweight or obesity in a subject, wherein the method comprises a step of orally administering a composition comprising an effective amount of a first agent capable of inducing satiety, and a second agent capable of augmenting the satiety-inducing effect of the first agent, and wherein the first and the second agent are optionally selected as described above. Moreover, the invention provides a method of treating or preventing overweight, obesity, or a disease or condition associated with overweight or obesity in a subject, which method is also characterised by a step of orally administering a composition comprising an effective amount of the first agent and of the second agent. Optionally said method comprises the oral administration of the particles and/or compositions at least once a day over a period of at least one week Of course, also the preferred particles and/or compositions as described above may therefore be used clinically, or as dietary supplements, for the prevention and/or treatment of obesity and overweight, as well as the prevention and/or treatment of diseases or conditions associated with obesity; e.g. by using the ingestible particles as defined herein and/or compositions comprising or prepared from a plurality of these particles for body weight reduction.

In other words, one aspect of the invention provides a method for the prevention and/or treatment of obesity and overweight, as well as the prevention and/or treatment of diseases or conditions associated with obesity, for appetite suppression, body weight reduction and/or for the induction of satiety, said method comprising a step of orally administering the particles of the invention and/or compositions comprising or prepared from a plurality of these particles. Optionally said method comprises the oral administration of the particles and/or compositions at least once a day over a period of at least one week.

In yet other words, one aspect of the invention provides the use of the particles of the invention and/or compositions comprising or prepared from a plurality of these particles in the manufacture of medicaments for the prevention and/or treatment of obesity and overweight, as well as the prevention and/or treatment of diseases or conditions associated with obesity, for appetite suppression, body weight reduction and/or for the induction of satiety. Optionally, this comprises the oral administration of the particles and/or compositions at least once a day over a period of at least one week.

As used herein, obesity is a medical condition in which excess body fat has accumulated to the extent that it may have an adverse effect on health. Overweight is understood as a borderline condition characterised by a body mass index (BMI) between 25 and below 30. Starting from a BMI of 30, the condition is classified as obesity.

In one embodiment, the particles and/or the compositions are administered to normal weight or overweight subjects gaining weight over time or otherwise being at risk of developing obesity. In this case, the therapeutic objective is to stop or limit the weight gain and prevent the development of obesity. Another purpose may be to reduce the risk that the subject develops a disease or condition associated with or caused by obesity.

In a further embodiment, the particles and/or the compositions are administered to obese patients in order to treat or reduce the severity of obesity. Again, the therapeutic use may also be directed to the reduction of the risk of developing a disease or condition associated with or caused by obesity.

A large number of diseases and conditions are nowadays considered to be associated with or caused by obesity, even though the mechanism by which they are linked to obesity may not always be fully understood. In particular, these diseases and conditions include—without limitation—diabetes mellitus type 2, arterial hypertension, metabolic syndrome, insulin resistance, hypercholesterolaemia, hypertriglyceridemia, osteoarthritis, obstructive sleep apnea, ischaemic heart disease, myocardial infarction, congestive heart failure, stroke, gout, and low back pain. The prevention and/or reduction of risk for developing any of these conditions falls within the scope of the therapeutic use according to the invention.

Moreover, the therapeutic use preferably involves the at least once daily oral administration of the particles and/or the compositions of the invention over a period of at least one week. In this context, the expression "therapeutic use" is understood to also cover the preventive or prophylactic use. In a further preferred embodiment, the particles and/or the compositions are administered to a human subject over a period of at least about 2 weeks, or at least about 4 weeks, or at least about 6 weeks, or at least about 2 months, respectively. Also preferred is an administration regimen providing for once or twice daily administration.

The time of administration should be selected to maximise the satiety-inducing effect on the amount of food which is subsequently taken up by the subject that is treated. For example, it is useful to administer a dose of the composition before a major meal, such as before a lunchtime meal and/or before the evening dinner such as to reduce the amount of food eaten during either of these meals. With respect to the precise timing, it is preferred that the dose is administered within about 5 minutes to 120 minutes prior to the respective meal, in particular about 10 minutes to about 120 minutes prior to the meal, or about 15 minutes to about 90 minutes prior to the meal, such as about 30 minutes or about 60 minutes prior to the meal.

In one embodiment, a dose comprising at least about 5 g of the fatty acid glyceride component is administered to a human subject at least once daily between about 15 minutes and about 90 minutes prior to a meal over a period of at least 4 weeks for the prevention and/or treatment of obesity or an associated disease.

The invention further provides a method of inducing satiety in a subject, or method of treating or preventing overweight, obesity, or a disease or condition associated with overweight or obesity in a subject, or method of controlling or reducing the body weight of a subject, each method comprising a step of orally administering a composition comprising an effective amount of a first agent capable of inducing satiety and a second agent capable of augmenting the satiety-inducing effect of the first agent, wherein the methods further comprise the use of a device for the collection, storage and/or display of information relating to a subject's adherence to, or the effectiveness of, a predefined therapeutic regimen of orally administering the composition.

According to a related aspect, the invention provides a body weight management system comprising the composition comprising effective amounts of the first agent and the second agent, and a device configured for the collection, storage and/or display of information relating to a subject's adherence, or the effectiveness of, a predefined therapeutic regimen of orally administering the composition.

In more detail, it is contemplated that the particles and/or the compositions of the invention are used in combination with the use of a device for the collection, storage and/or display of information relating to a subject's adherence to the therapy and/or the effectiveness of the therapy. As used herein, information relating to a subject's adherence to the therapy may include, for example, information on whether a dose was administered within a certain period of time (e.g. during a calendar day), or the time at which each dose was administered. The device is preferably a programmed electronic device, such as a computer, in particular a microcomputer, and most preferably a portable microcomputer such as a mobile phone ("smartphone"), or a wearable device such as a smart watch, an electronic wristband, or the like. The information may be received by the device automatically from a sensor, or it may be entered manually by a user, such as the subject or patient, the physician, nurse, or by a caregiver, and stored for subsequent analysis or display. For example, the patient may periodically monitor his or her actual compliance or adherence to the therapy.

The device may be programmed to provide the user with a feedback signal or reminder in case of non-compliance or lack of adequate adherence to the therapy. The feedback signal may be optical, haptic (e.g. vibration), or acoustic.

Information relating to the effectiveness of the therapy may include, for example, the weight of the subject, the degree of hunger or appetite, the number of meals and snacks, or the type or amount of food eaten during any particular period of time (e.g. a calendar day), or even physiological data such as the blood glucose concentration or blood pressure. Depending on its type, the information relating to the effectiveness of the therapy may be automatically received by the device or entered manually by the user. Information with respect to the feeling of satiety or hunger may be usefully entered by the user or patient in a manual mode, whereas physiological parameters such as blood glucose or blood pressure may be received from the respective measuring devices used for their determination. In the latter case, the transfer of the data encoding the information generated by the measuring device to the device for the storage and/or display of the information is preferably wireless.

In more detail, information collection may be user-initiated or the device may be programmed with an application (i.e. software) which creates an alert calling for the user to input her or his satiety-state information. Preferably, information collection proceeds in regular time intervals such as 15 min or 30 min intervals. In one embodiment, information collection is performed throughout a period of 12, 16 or 18 hours per day. In another embodiment, information collection is performed in multiple periods of for instance 1 to 3 hours over the day, for instance three times for 3 hours each. Preferably such time periods cover meal times such as breakfast, lunch and dinner. Preferably, users—for a given period of information collection—may not refer to previous satiety ratings when providing the real-time information.

Information collection may proceed in the following fashion. After the user has opened the software application, a satiety state screen is displayed on the colour touch screen using visual analogue scales for the assessment of satiety. Such scales and scores have previously been described in detail 8 lint A, Raben A, Blundell J E, Astrup A. Reproducibility, power and validity of visual analogue scales in assessment of appetite sensations in single test meal studies. Int J Obes Relat Metab Disord 2000; 24:38-48). In brief, the visual analogue scale (VAS) consists of a horizontal, unstructured, 10 cm line with words anchored at each end, describing the extremes ('not at all' or 'extremely') of the unipolar question, 'How satiated are you right now?' To ensure reliable and valid results, participants rate their feeling of satiation as precisely as possible, and they cannot refer to their previous ratings when marking the VAS.

The satiety state screen may display a query 1 "how hungry do you feel?" combined with an unstructured sliding scale labelled "I am not hungry at all" on one end to "very hungry" on the other hand. The application will wait for the user to touch the sliding scale at one position. Upon touching the scale, a slider may appear, and the user may adjust its position. The application will determine the position of the slider after the user removed its touching finger from the slider symbol, retrieve the positional value and use it for further processing.

Further potentially useful embodiments are easily derivable on the basis of the guidance provided herein-above and the following examples.

EXAMPLES

Example 1: Particle Integrity Assay

PromOat® beta-glucan was from Tate&Lyle, Sweden. Inulin was from Spinnrad, Germany. Benefiber® resistant dextrin (also known as Benefiber® Nutriose®) was from Novartis, UK. Nutriose® FB resistant dextrin and Nutralys® S85F (a pea protein) were obtained from Roquette, France. Unisol DP (a soy protein with a protein content of approx. 90%) was obtained from Vitablend, Netherlands.

Palm stearin and Omega-3 fat powder were from Bressmer, Germany. Prifex® 300 palm stearin was from Unimills, The Netherlands. Plant-derived Omega-3-Concentrate powder 67 and Omega-3-Concentrate oil based on linseed oil were from Bressmer, Germany. Safflower oil was from Brökelmann, Germany.

Granules were prepared by melting one lipid (e.g. at 50° C. to 70° C.) and optionally adding other lipid components and a few crystals of Oil Red 0 (Sigma Aldrich, USA) to obtain a homogenous melt or suspension. For test samples polymer(s) were incorporated by mechanical mixing. Each composition was transferred into a zip-loc-bag and cooled to −18° C. in a freezer. The material was first crushed by means of a hammer, shredded to a granulate in a kitchen blender (Bosch ProfiMIXX, Germany), optionally dried under vacuum at 25° C. and then classified through a set of wire mesh sieves (VWR International, Germany) to a granulate size of below 2.0 mm and above 1.3 mm.

Fresh pork stomach (from a local butcher) was cut into 3 cm×3 cm pieces and placed into the bottom of a glass petri dish (10 cm diameter). 22 mL fasted-state simulated gastric fluid (FaSSGF) were added to the petri dish. FaSSGF was prepared by dis-solving 1 g of NaCl (Sigma-Aldrich) in 450 mL of water, adding 30 mg of SIF powder (biorelevant.com), adjusting the pH to 2.0 with 0.1 N HCl (Sigma-Aldrich) and adding water to a final volume of 500 mL. The petri dish was covered and placed onto a petri dish shaker (ST5 from CAT, Germany) set to a tilt angle of 12° and a speed of 50/min. The shaker was placed into an oven heated to a temperature of 37° C. After 30 minutes, 350 mg granulate were added to the contents of the petri dish without interrupting agitation. After 5 min, the samples were removed from the oven, and the piece of pork stomach was rinsed three times with water (3 mL each). Any material bound to the stomach surface was removed by means of a spatula, transferred into a weighing dish, and dried to constant weight (electronic moisture meter MLB 50-3N, Kern & Sohn, Germany). This dry weight, which at least in parts reflects the weight of potentially present mucoadhesive material, was recorded and calculated as percent of initial granulate weight, representing binding as a measure of mucoadhesiveness.

For determining the particle integrity, the petri dish containing the remaining unbound material was agitated at 37° C. for another 15 min, and particle integrity was classified by visual inspection as "low" (complete disintegration or disintegration of at least 50% of the particles), or "high" (disintegration of less than 50% of the particles) or "medium" (disintegration of less than 50% of the particles, but visible loss of small amounts of powders from the particles).

In result, it was found that most test compositions with particles according to the invention showed high particle integrity with no or almost no mucoadhesion, as shown in the table below.

| Sample | Glyceride (g) | Polysaccharide (g) | Binding | Integrity |
| --- | --- | --- | --- | --- |
| Test 1 | Palm stearin, 5 g | Benefiber, 5 g | 0% | high |
| Test 2 | Prifex 300, 5 g | Benefiber, 5 g | 0% | high |
| Test 3 | Prifex 300, 4 g<br>Safflower oil, 2 g | Benefiber, 6 g | 0% | high |

-continued

| Sample | Glyceride (g) | Polysaccharide (g) | Binding | Integrity |
|---|---|---|---|---|
| Test 4 | Palm stearin, 5 g | Inulin, 5 g | n.d. | high |
| Test 5 | Palm stearin, 5 g | Benefiber, 2 g<br>PromOat, 2 g | n.d. | medium |
| Test 6 | Prifex 300, 6 g | PromOat, 5 g | 0% | high |
| Test 7 | Prifex 300, 4 g<br>Safflower oil, 2 g | Konjac glucomannan, 1 g<br>PromOat, 4 g | 0% | medium |
| Test 8 | Prifex 300, 6 g | Konjac glucomannan, 1 g<br>Benefiber, 2 g<br>PromOat, 2 g | 0% | high |
| Test 9 | Prifex 300, 4 g<br>Omega-3-Concentrate powder 67, 3 g | Benefiber, 3 g | 0% | high |
| Test 10 | Prifex 300, 4 g<br>Safflower oil, 1 g<br>Omega-3-Concentrate powder 67, 1.5 g | Benefiber, 4.5 g | 0% | high |
| Test 11 | Prifex 300, 6 g | Konjac glucomannan, 1 g<br>Benefiber, 2 g | 0% | high |
| Test 12 | Prifex 300, 9 g<br>Omega-3-Concentrate oil, 1 g | Nutriose FB, 10 g | n.d. | high |
| Test 13 | Prifex 300, 7 g<br>Safflower oil, 2 g<br>Omega-3-Concentrate oil, 1 g | Nutriose FB, 10 g | n.d. | high |
| Test 14 | Prifex 300, 8 g<br>Omega-3-Concentrate oil, 2 g | Nutriose FB, 10 g | n.d. | high |
| Test 15 | Gelucire 43/10, 10 g | Nutriose FB, 10 g | n.d. | high |
| Test 16 | Prifex 300, 10 g | Nutralys S85F, 5 g<br>Nutriose FB, 5 g | n.d. | medium |
| Test 17 | Prifex 300, 10 g | Nutralys S85F, 4 g<br>Nutriose FB, 6 g | n.d. | medium |
| Test 18 | Prifex 300, 10 g | Nutralys S85F, 3 g<br>Nutriose FB, 7 g | n.d. | medium |
| Test 19 | Prifex 300, 10 g | Unisol DP, 5 g<br>Nutriose FB, 5 g | n.d. | high |
| Test 20 | Prifex 300, 10 g | Unisol DP, 4 g<br>Nutriose FB, 6 g | n.d. | high |
| Test 21 | Prifex 300, 9 g<br>Omega-3 oil, 1 g | Unisol DP, 5 g<br>Nutriose FB, 5 g | n.d. | medium |

Example 2: Breath Tests on Healthy Volunteers

Gastrointestinal half-life and bioavailability of free fatty acids were assessed using the $^{13}$C-octanoic acid breath test. The labelled octanoic acid substrate is rapidly absorbed in the intestine and metabolised in the liver with the production of $^{13}CO_2$, which is exhaled, thus reflecting uptake of octanoic acid from the gastrointestinal tract and after exit from the stomach. At the beginning of the experiment a reference breath sample was taken from the subject. Subsequently, the subject consumed a load of either lipid granulate as reference sample, or lipid granulate containing the polysaccharides as test sample.

Prifex® 300 palm stearin was from Unimills, The Netherlands. Benefiber® resistant dextrin (also known as Benefiber® Nutriose®) was from Novartis, UK.

Granulate was prepared by melting lipid at 50° C. and adding 100 mg of $^{13}$C octanoic acid (Campro Scientific, The Netherlands), and—for test samples—incorporating polymer. The mixture was subsequently transferred into a ziploc-bag and cooled to −18° C. in a freezer. The material was crushed by means of a hammer, shredded to a granulate in a kitchen blender (Bosch, Germany), dried under vacuum at 25° C. and classified through a set of wire mesh sieves (VWR International, Germany) to a granulate size of below 1.3 mm and above 0.5 mm.

For sample ingestion, frozen granulate was mixed with 100 g cold yogurt (fruit flavour, ca. 100 calories) and consumed within one to two minutes. After ingesting the samples, subject exhaled through a mouthpiece to collect an end-expiratory breath sample into a 300 mL foil bag at time intervals. Breath samples were taken over a period of 410 min. During this time period, 0.5-1.0 L of water were drunk at a rate of approximately one glass per hour, a light lunch was consumed after 180 min, and physical exercise represented daily routine.

After completion of breath bag collection, analysis was performed by means of a FANci2 breath test analyser based on non-dispersive infrared spectroscopy (Fischer Analysen Instrumente GmbH, Germany). $^{13}$C abundance in breath was expressed as relative difference (‰) from the universal reference standard (carbon from Pee Dee Belemnite limestone). $^{13}$C enrichment was defined as the difference between $^{13}$C abundance in breath prior to sample ingestion and $^{13}$C abundance at the defined time points after sample ingestion and was given in delta over basal (DOB, ‰). From the breath test analyser's operating software (FANci version 2.12.42.14 02/14), values of cumulated percent dose rate (cPDR, corresponding to bioavailability) were taken to protocol.

As shown in the table below, it was found that the particles of test composition 1 lead to an increase in bioavailability of the fatty acid, as measured by the breath test (see cPDR), which effect is due to the combination of the glyceride component with the resistant dextrin. This in turn, has resulted in increased satiety in human volunteers.

| Sample | Fatty acid glyceride | Polysaccharide | cPDR (%) |
|---|---|---|---|
| Reference 1 | Prifex 300: 6 g | — | 29.0 |
| Test composition 1 | Prifex 300: 6 g | Benefiber: 6 g | 78.2 |

Example 3: Exemplary Edible Particles

Composition 3.1:

2 kg of a premix were prepared in batches. For each batch, 0.5 kg palm stearin (Prifex® 300, Brenntag B.V., Belgium) and 0.2 kg safflower oil (Bressmer, Germany) were brought to a melt in a cooking pot over an induction plate. When the melt had a temperature of 60° C., 0.7 kg resistant dextrin (Nutriose® FB06, Barentz, Netherlands) and 0.3 kg soy protein (Unisol DP IP Non GMO, Barentz, Netherlands) were incorporated by means of a cooking spoon. The mixture was transferred in aliquots into zip-loc plastic bags and cooled to room temperature to form solid plates. Lipid-polymer plates were further cooled in a fridge set at 8° C. and then shredded to particles of approx. 5 mm and smaller by means of a blender (Vitamix® Professional 750, Vita-Mix Corp., USA). The obtained premix was fed via a volumetric dosing system (Dosimex DO-50, Gabler GmbH & Co KG, Germany) into a powder inlet of a twin screw extruder (Extruder DE-40/10, Gabler GmbH & Co KG, Germany) operating at 15 rpm and extruded at a temperature range of approx. 20° C. to strands of 1.0 mm diameter. Extruded strands were cut to granules of 0.8 mm to 2.5 mm length by means of rotating blades running at 250 rpm. Subsequently, the extrudate was classified on a sieving machine (Siftomat 1, Fuchs Maschinen AG, Switzerland) to collect granules of 1-2 mm.

Composition 3.2:

550 g palm stearin (Prifex® 300 from Unimills, The Netherlands) were brought to 60° C. to obtain a homogenous melt. 550 g resistant dextrin (Nutriose® FB06, Barentz, Germany) were incorporated by mechanical mixing. The composition was transferred into zip-loc-bags and cooled to −18° C. in a freezer. The material was first crushed by means of a hammer and then shredded to a granulate in a kitchen blender (Bosch ProfiMIXX, Germany or Vitamix® Professional 750, Vita-Mix Corp, USA), and classified through a set of wire mesh sieves (VWR International, Germany) to a granulate size of below 2.0 mm and above 1.3 mm.

Composition 3.3:

550 g palm stearin (Prifex® 300 from Unimills, The Netherlands) were brought to 60° C. to obtain a homogenous melt. A binary mixture of 275 g soy protein concentrate (Unisol DP IP, Vitablend, The Netherlands) and 275 g resistant dextrin (Nutriose® FB 06, Barentz, Germany) was incorporated by mechanical mixing. The composition was transferred into zip-loc-bags and cooled to −18° C. in a freezer. The material was first crushed by means of a hammer and then shredded to a granulate in a kitchen blender (Bosch ProfiMIXX, Germany or Vitamix® Professional 750, Vita-Mix Corp, USA), and classified through a set of wire mesh sieves (VWR International, Germany) to a granulate size of below 1.0 mm.

The invention claimed is:

1. An oral composition comprising a plurality of edible particles comprising
    (a) a first agent capable of inducing satiety,
    (b) a second agent capable of augmenting the satiety-inducing effect of the first agent,
  wherein the first agent is a medium or long chain fatty acid compound, said fatty acid compound being comprised in a fatty acid glyceride component, wherein the second agent is a water-soluble polysaccharide component, wherein the polysaccharide component is embedded in the fatty acid glyceride component, wherein the polysaccharide component and the fatty acid glyceride component are inseparably blended into one coherent solid phase, and wherein the particles comprise not more than 5 wt.-% of mucoadhesive polymer.

2. The composition of claim 1, wherein the second agent increases the bioavailability of the first agent.

3. The composition of claim 1, wherein the second agent prolongs the integrity of the particles and/or accelerates the gastric emptying of the particles after oral administration of the composition.

4. The composition of claim 1, wherein the fatty acid glyceride component has a melting point of higher than 37° C.

5. The composition of claim 1, wherein the second agent is a water-soluble polysaccharide component based on glucose or fructose having an average degree of polymerisation from 2 to 100, or from 4 to 80.

6. The composition of claim 1, wherein the water-soluble polysaccharide component comprises a neutral polysaccharide that is resistant to digestion in the human small intestine.

7. The composition of claim 1, wherein the water-soluble polysaccharide component exhibits a solubility of at least 2 wt.-%, and optionally of at least 5 wt.-%, measured in purified water at 25° C.

8. The composition of claim 1, wherein the edible particles have a sieve diameter in the range from 0.01 mm to 10 mm and comprise an intimate mixture of
    (a) at least 10 wt.-% of a water-soluble polysaccharide component based on glucose or fructose having an average degree of polymerisation from 2 to 100, or from 4 to 80, and
    (b) at least 10 wt.-% of a fatty acid glyceride component having a melting point of higher than 37° C.

9. The composition of claim 1, wherein the weight ratio of the medium or long chain fatty acid compound to the water-soluble polysaccharide component is in the range from 0.5 to 5.

10. The composition of claim 1, wherein the mucoadhesive polymer is selected from poly(carboxylates), poly(methacrylic acid), copolymers of acrylic and methacrylic acid, poly(hydroxyethyl methacrylic acid), alginic acid or salts thereof, pectins, cellulose ethers, mucoadhesive polysaccharides like chitosan, gellan gum, guar gum, or xanthan gum, and gum arabic.

11. The composition of claim 1, wherein the particles are free of a synthetic drug substance.

12. The composition of claim 1, wherein the fatty acid compound is a free fatty acid, a salt of a fatty acid, or an esterified fatty acid, and wherein the esterified fatty acid is a monoglyceride, diglyceride or triglyceride.

13. The composition of claim 1, wherein the composition is provided in single dose units or packages, wherein the amount of the composition is from 3 g to 20 g, and/or wherein the amount of the fatty acid glyceride component in the composition is at least 1 g.

14. A method of controlling or reducing the body weight of a subject, said method comprising a step of orally administering the composition of claim 1.

15. A method of inducing satiety in a subject, said method comprising a step of orally administering the composition of claim 1.

16. The method of claim 15, wherein the subject is a human subject having developed a disease selected from the group of obesity, diabetes mellitus type 2, arterial hypertension, metabolic syndrome, insulin resistance, hypercholesterolaemia, hypertriglyceridaemia, osteoarthritis, obstructive sleep apnea, ischaemic heart disease, myocardial infarction, congestive heart failure, stroke, gout, and low back pain.

17. The method of claim 15, wherein the oral administration of the composition is performed at least once a day over a period of at least one week.

18. The method of claim 15, further comprising the use of a device for the collection, storage and/or display of information relating to a subject's adherence to, or the effectiveness of, a predefined therapeutic regimen of orally administering the composition.

19. A body weight management system comprising a device configured for the collection, storage and/or display of information relating to a subject's adherence, or the effectiveness of, a predefined therapeutic regimen of orally administering the composition of claim 1.

* * * * *